United States Patent
Gante et al.

(10) Patent No.: US 6,455,529 B1
(45) Date of Patent: Sep. 24, 2002

(54) ADHESION RECEPTOR ANTAGONISTS

(75) Inventors: Joachim Gante, Darmstadt; Hörst Juraszyk; Peter Raddatz, both of Seeheim; Hanns Wurziger, Darmstadt; Sabine Bernotat-Danielowski, Bad Nauheim; Guido Melzer, Hofheim/Ts, all of (DE)

(73) Assignee: Merck Patent Gesellschaft mit beschraenkter Haftung (DE)

( * ) Notice: Subject to any disclaimer, the term of this patent is extended or adjusted under 35 U.S.C. 154(b) by 1100 days.

(21) Appl. No.: 08/642,268

(22) Filed: May 3, 1996

(30) Foreign Application Priority Data

May 5, 1995 (DE) .......................... 195 16 483

(51) Int. Cl.⁷ ................. A61K 31/496; A61K 31/4439; C07D 413/06
(52) U.S. Cl. .............................. 514/253.1; 514/254.02; 514/326; 514/221; 514/252.11; 514/253.01; 514/316; 514/330; 514/331; 514/392; 514/424; 514/616; 544/364; 544/369; 544/357; 544/360; 546/209; 546/191; 546/226; 546/231; 548/229; 548/230; 548/232; 548/550; 540/513
(58) Field of Search ................ 544/369, 364; 546/209; 548/229; 514/252, 326, 253.1, 254.02

(56) References Cited

U.S. PATENT DOCUMENTS

| | | | |
|---|---|---|---|
| 5,053,393 A | 10/1991 | Tjoeng et al. | 514/18 |
| 5,084,466 A | 1/1992 | Alig et al. | 514/353 |
| 5,256,812 A | 10/1993 | Alig et al. | 560/35 |
| 5,344,957 A | * 9/1994 | Bovy | 560/35 |
| 5,399,585 A | 3/1995 | Alig et al. | 514/438 |
| 5,442,064 A | 8/1995 | Pieper et al. | 544/360 |
| 5,532,255 A | * 7/1996 | Raddatz et al. | 544/369 |
| 5,561,148 A | 10/1996 | Gante et al. | 514/376 |
| 5,614,535 A | * 3/1997 | Juraszyk et al. | 544/369 |
| 5,627,197 A | * 5/1997 | Gante et al. | 544/369 |

FOREIGN PATENT DOCUMENTS

| | | |
|---|---|---|
| CA | 2 043 317 | 11/1991 |
| EP | 462960 | 12/1991 |
| EP | 0 542 363 | 5/1993 |
| EP | 623615 | 11/1994 |
| WO | 93/00095 | 1/1993 |
| WO | 94/14776 | 7/1994 |
| WO | 65/18111 | 7/1995 |
| WO | 65/18619 | 7/1995 |

OTHER PUBLICATIONS

Bovy et al, *Bioorganic & Medicinal Chemistry*, vol. 2, No. 9, p 881–895 (1994).*
Smith et al, *J. Biol. Chem.* 265, p 12267–12271 (1990).*
Müller et al, in *Receptor Data For Biological Experiments*, Chapter 20, p112–117 (1991).*
Bondinell et al., "Design of a Potent and Orally Active Nonpeptide Platelet Fibrinogen Receptor (GPIIb/IIIa) Antagonist", *Bioorganic & Medicinal Chemistry*, vol. 2, No. 9, pp. 897–908 (1994).
Nicholson et al., "SC–54684A: An Orally Active Inhibitor of Platelet Aggregation", *Circulation*, vol. 91, No. 2, Jan. 15, 1995; p403.
Zablocki et al., "Potent in Vitro and in Vivo Inhibitors . . . ", *J. Med. Chem.*, pp. 2378–2394 (1995).
Ku et al., Potent Non–peptide Fibrinogen Receptor . . . , *J. Med. Chem.*, 38, pp. 9–12 (1994).
Carteaux et al., "Ro 44–9883, a New Non–Peptide GPIIb–GBIIIa Antagonist . . . ", *Thrombosis and Haemostasis*, 70 (5), pp. 817–821 (1993).
Alig et al., "Low Molecular Weight, Non–Peptide Fibrinogen Receptor Antagonists", *J. Med. Chem.*, 35, pp. 4393–4407.
Ku et al., "Direct Design of a Potent Non–Peptide Fibrinogen Receptor Antagonists . . . ", *Am. Chem. Soc.*, 115, pp. 8861–8862 (1993).
Eldred et al., "Orally Active Non–Peptide Fibrinogen Receptor . . . ", *J. Med. Chem.*, 37, 3882–3885 (1994).

* cited by examiner

*Primary Examiner*—Emily Bernhardt
(74) *Attorney, Agent, or Firm*—Millen, White, Zelano & Branigan, P.C.

(57) ABSTRACT

Compounds of the formula I

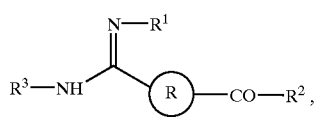

in which $R^1$, $R^2$ and $R^3$ have the stated meanings, and their physiologically acceptable salts, inhibit the binding of fibrinogen to the corresponding receptor and can be used for the treatment of thromboses, osteoporoses, oncoses, stroke, myocardial infarct, ischemias, inflammations, arteriosclerosis and osteolytic disorders.

17 Claims, No Drawings

ADHESION RECEPTOR ANTAGONISTS

The invention relates to novel adhesion receptor antagonists of the formula I

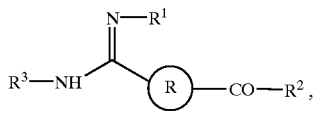

in which
R is

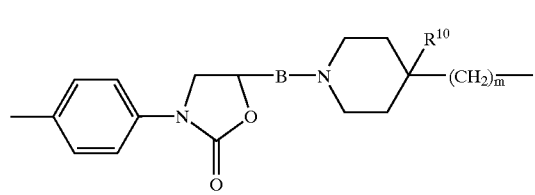

with
B=$CH_2$, CO or CS, $R^{10}$=OH or H and
m=0, 1, 2, 3 or 4;

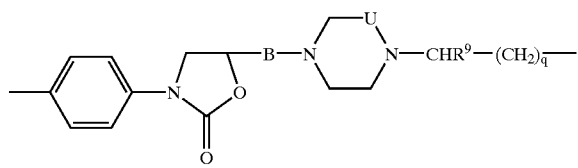

with
B=$CH_2$, CO or CS, U=$CH_2$ or CO,
$R^9$=H, $CO_2H$ or $CO_2A$ and q=0, 1, 2 or 3;

(c)

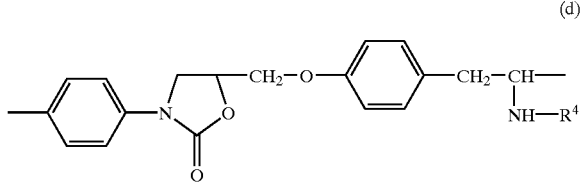

with
n=1, 2, 3 or 4;

(d)

with $R^4$=H, A—$SO_2$, Ar—$SO_2$, A—CO, Ar—CO or Het—CO;

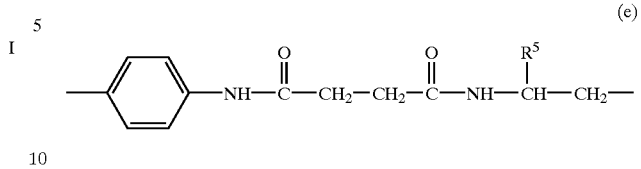

with
$R^5$=H, A, alkynyl or alkenyl with in each case 2–5 C atoms, or Ar;

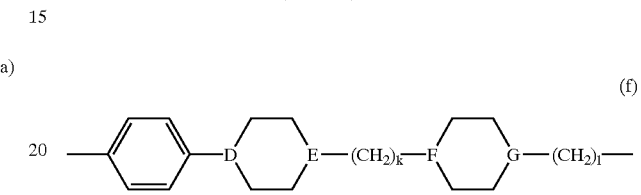

with
D, E, F and G each, independently of one another, CH or N and
k and 1 each, independently of one another, 0, 1, 2, 3 or 4, where k=0 is excluded when E and F are each N and 1=0 is excluded when G=N;

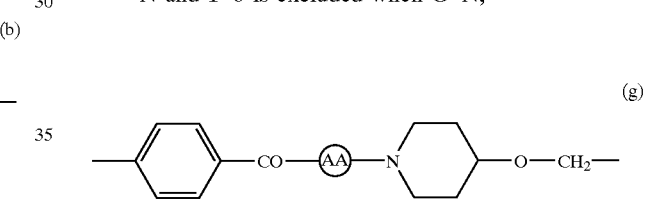

where AA is an amino acid residue selected from a group consisting of residues of Ala, Arg, Asn, Asp, Cys, Gln, Glu, Gly, His, Ile, Leu, Lys, Met, Phe, Pro, Ser, Thr, Trp, Tyr or Val, which is bonded by peptide linkages;

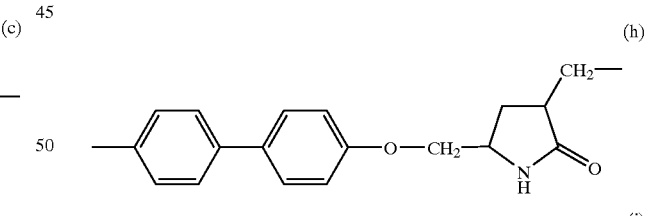

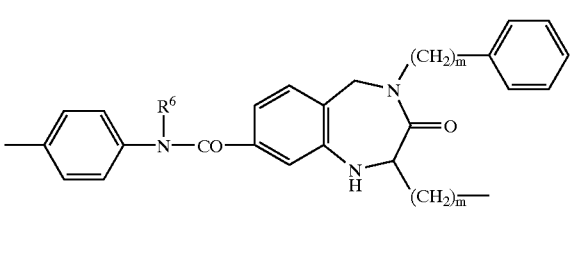

with
$R^6$=H or A and
m in each case independently of one another 0, 1, 2, 3 or 4;

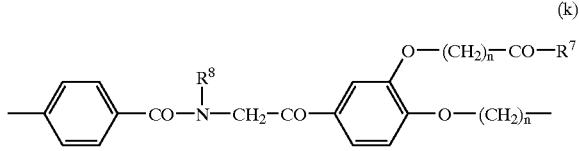

with
R⁷=OH, OA, OAr, OHet, NHOH, NH₂, NHA or NA₂,
R⁸=H or A and
n in each case independently of one another 1, 2, 3 or 4; or

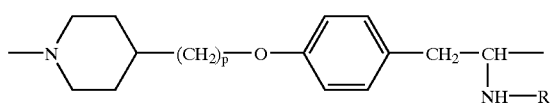

where $R^4$ has the meaning already indicated under (d), and p is 2, 3, 4, 5 or 6;

$R^1$ is H, A, Ar—CO, A—CO, OH, OA or AO—CO;

$R^2$ is OH, OA, OAr, OHet, NHOH, NH₂, NHA or NA₂;

$R^3$ is A—CO, Ar—CO, Het—CO, Het—O—CO, Ar—O—CO, A—O—CO, Ar—SO₂ or A—SO₂;

A is alkyl with 1 to 6 C atoms;

Ar is aryl of 6 to 10 C atoms, e.g., phenyl, naphthyl, or diphenylmethyl or benzyl, which are unsubstituted or substituted once, twice or three times by A, F, Cl, Br, I, OA, —O—CH₂—O—, COOA, COOH, CF₃, OH, NO₂, CN, O—CO—A, NH₂, NHA or NA₂, and Het is a mono- or binuclear saturated, unsaturated or aromatic heterocycle with 1 to 4 N, O and/or S atoms, which can be unsubstituted or substituted once by F, Cl, Br, CF₃, A, OH, OA, CN or NO₂, and their physiologically acceptable salts and solvates.

Similar compounds are disclosed in EP-A1-0 623 615 (DE 43 14 378).

The invention has an object of finding novel compounds with valuable properties, in particular those which can be used to produce pharmaceuticals.

Upon further study of the specification and appended claims, further objects and advantages of this invention will become apparent to those skilled in the art.

This object has been achieved by the invention. It has been found that the compounds of the formula I and their solvates and salts have valuable pharmacological properties while being well tolerated. In particular, they act as integrin inhibitors, and they inhibit, in particular, the interactions of the β₃ or β₅ integrin receptors with ligands. The compounds show particular activity in the case of the integrins α,β₃, α,β₅ and α_{IIb}β₃. This effect can be demonstrated, for example, by the method described in J. W. Smith et al. in J. Biol. Chem., 2265, 12267–12271 (1990). In particular, they inhibit the binding of fibrinogen, fibronectin and von-Willebrand factor to the fibrinogen receptor of blood platelets (glycoprotein IIb/IIIa) and the binding thereof and of other adhesive proteins, such as vitronectin, collagen and laminin, to the corresponding receptors on the surface of various types of cells. The compounds thus influence cell-cell and cell-matrix interactions. They prevent, in particular, the development of blood platelet thrombi and can therefore be used for the treatment of thromboses, stroke, myocardial infarct, angina pectoris, osteolytic disorders, especially osteoporosis and restenosis after angioplasty, ischemias, inflammations, arteriosclerosis and acute kidney failure, for example. The compounds inhibit or prevent vessel development and thus also show an antiangiogenetic effect. The compounds furthermore have an effect on tumor cells by inhibiting metastasis thereof. They can thus also be used as antitumor agents.

There is evidence that tumor cells gain access to vessels through microthrombi and thus are protected from detection by the cells of the immune system. Likewise, microthrombi act to assist the binding of tumour cells to vessel walls. Since the formation of microthrombi is connected with the binding of fibrinogen to the fibrinogen receptor (glycoprotein IIb/IIIa), fibrinogen binding inhibitors are regarded as also being metastasis inhibitors. Their antiangiogenetic capabilities mean that they prevent tumor cells from being supplied with blood and nutrients.

The compounds are additionally suitable as antimicrobial agents which are able to prevent infections like those caused, for example, by bacteria, fungi or yeasts. The substances can therefore be preferably given as concomitant antimicrobial agents when interventions are performed on organisms in which exogenous substances such as, for example, biomaterials, implants, catheters or cardiac pacemakers are inserted. They act as antiseptics. Antimicrobial activities of the compounds can be demonstrated, for example, by the method of P. Valentin-Weigand et al., described in Infection and Immunity, 2851–2855 (1988).

The other properties of the compounds can be demonstrated by methods described in EP-A1-0 462 960. Inhibition of the binding of fibrin to the fibrinogen receptor can be demonstrated by the method indicated in EP-A1-0 381 033. The platelet aggregation inhibiting effect can be demonstrated in vitro by the method of Born (Nature 4832, 927–929, (1962)).

The invention furthermore relates to a process for the preparation of a compound of the stated formula I and of its salts, characterized in that (i) a compound of the formula I is liberated from one of its functional derivatives by treatment with a solvolyzing or hydrogenolyzing agent, or in that (ii) a compound of the formula II

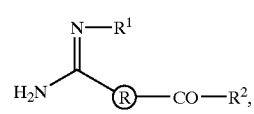

in which
R, $R^1$ and $R^2$ have the stated meanings, is reacted with a compound of the formula III

R³—X        III, in which
$R^3$ has the stated meaning, and
X is OH, F, Cl, Br, I or another easily displaceable leaving group, or in that (iii) to prepare a compound of the formula I with R=(a), (b), (c) or (d), a compound of the formula IV

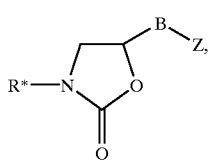

above,
R* is

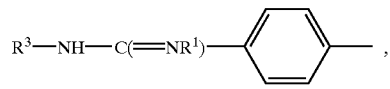

where $R^1$ and $R^3$, as well as B, have the meanings stated above, and
Z is Cl, Br, I, OH or a reactively esterified OH group,
is reacted with a compound of the formula Va

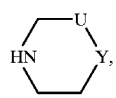

in which
Y is $-CH-(CH_2)_m-COR^2$, $-N-CHR^9-(CH_2)_q-COR^2$ or $-N-(CH_2)_n-COR^2$, where U, $R^2$, $R^9$, m, q and n have the meanings stated above,
or with a compound of the formula Vb

in which
L is $-(CH_2)_n-COR^2$ or $-CH_2-CH(NHR^4)-COR^2$, where $R^2$, $R^4$ and n have the meanings stated above, and
X' is OH or a salt-like radical which can be derived from OH, or in that
a compound of the formula VI

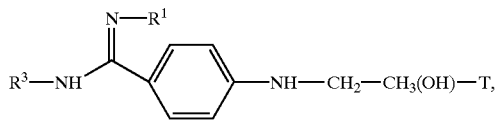

in which
T is

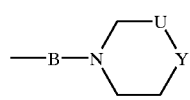

or

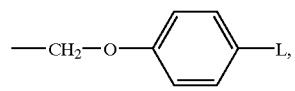

where B, L, U and Y, and
$R^1$ and $R^3$ have the meanings already stated, is reacted with a reactive derivative of carbonic acid, or in that
(iv) to prepare a compound of the formula I with R=(e), (f), (g), (h), (i) or (k), a compound of the formula VII

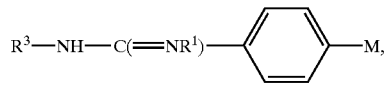

in which
$R^1$ and $R^3$ have the meanings already stated, and
M is

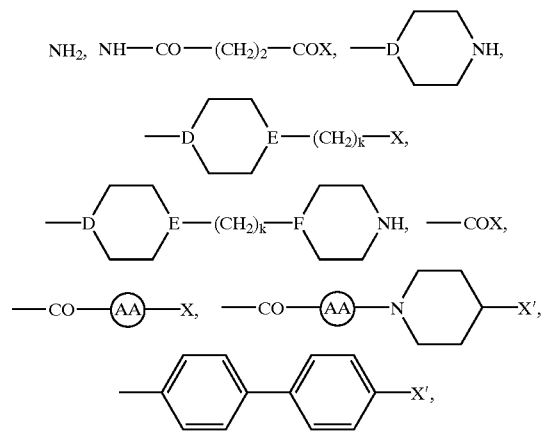

$-NR^6H$ or $-CONR^8H$, where D, E, F, X, X', AA, $R^6$, $R^8$ and k have the meanings already stated,
is reacted with a compound of the formula VIII $R^2-CO-Q$      VIII, in which
$R^2$ has the stated meaning, and
Q is
$-CH_2-CHR^5-NHCO-(CH_2)_2-COX$, $-CH_2-CHR^5-NH_2$,

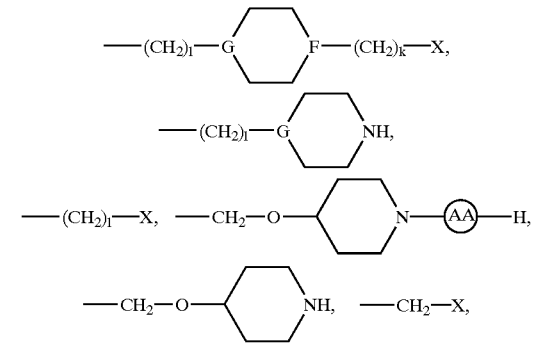

-continued

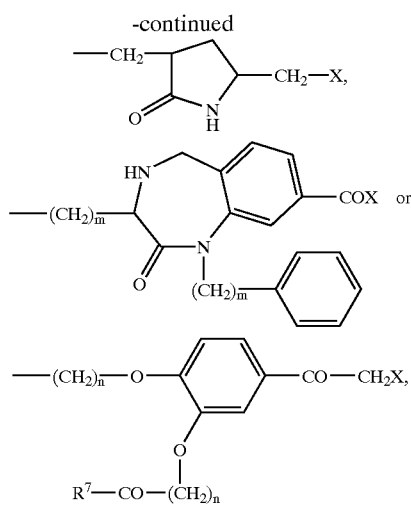

where F, G, X, $R^5$, $R^7$, AA, k, l, m and n have the meanings already stated, or in that (v) to prepare a compound of the formula I with R=(1), a compound of the formula IX

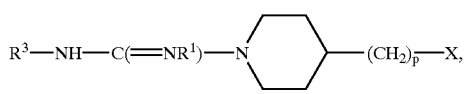   IX in which
$R^1$, $R^3$, X and p have the stated meanings,
is reacted with a compound of the formula X

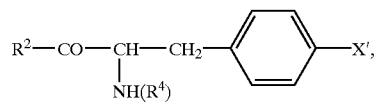   X in which
$R^2$, $R^4$ and X' have the stated meanings,
or in that to prepare a compound of the formula I, in a compound which corresponds per se to the formula I (vi) a radical $R^1$ is converted into a different radical $R^1$ by alkylation or acylation, or in that (vii) a radial $R^2$ is converted into a different radical $R^2$ by alkylation of an amide
complete or partial hydrolysis of a cyano group
esterification of a COOH group or
conversion of a COOH or COOA group into an amide, or in that (viii) a compound of the formula I according to claim 1 is converted by treatment with an acid or base into one of its salts.

The compounds of the formula I have at least one chiral center and may therefore exist in several enantiomeric forms. All these forms (for example R and S forms) and mixtures thereof (for example the RS forms) are included in the formula I.

Hereinbefore and hereinafter, all radicals and parameters have the meanings stated for formulae I to X unless expressly stated otherwise. If a plurality of groups or parameters with the same symbols are present in the molecule, they may, independently of one another, assume different definitions.

The group A in the above formulae has 1–6, preferably 1, 2, 3 or 4, C atoms. Specifically, A is preferably methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl.

The radical

is particularly preferably

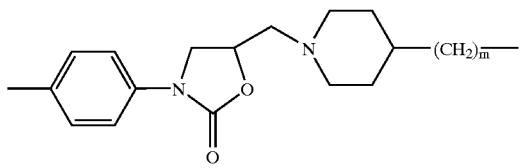

with m=0 or 1 or

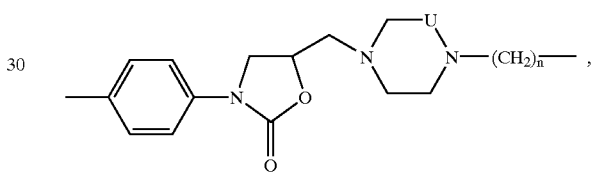

with
U=CO or $CH_2$ and
n=1 or 2
but furthermore also preferably

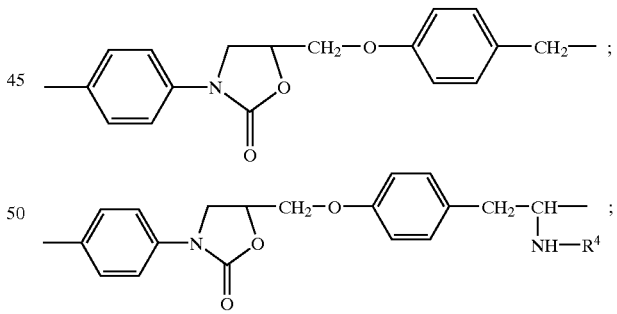

with $R^4$=H, A—$SO_2$ or Ar—$SO_2$;

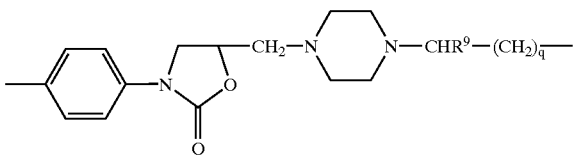

with
q=1 or 2 and

R=COOH, COOA or H;

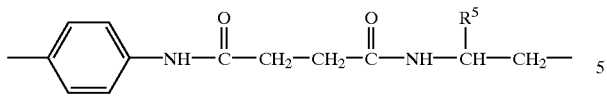

with R⁵=H, A, alkynyl or alkenyl with 2–4 C atoms or Ar;

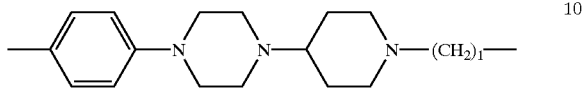

with l=1 or 2;

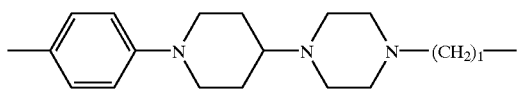

with l=1 or 2;

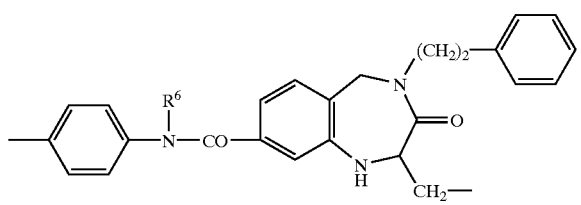

with R⁶=H or A;

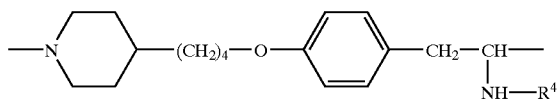

with R⁴=SO₂A or

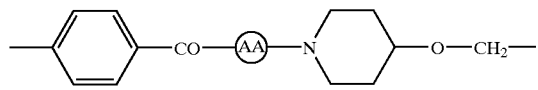

where AA is an amino acid residue selected from a group consisting of residues of Ala, Arg, Asn, Asp, Cys, Gln, Glu, Gly, His, Ile, Leu, Lys, Met, Phe, Pro, Ser, Thr, Trp, Tyr or Val, which is bonded via peptide linkages.

R¹ is preferably hydrogen, methyl or ethyl.

R² is preferably OH or OA, but also preferably phenyl—CH₂—O—(benzyloxy), while R³ is preferably A—CO, Ar—CO, Het—CO, Ar—O—CO, Ar—SO₂ or A—SO₂.

Ar is preferably phenyl, benzyl or diphenylmethyl, but furthermore also preferably 1- or 2-naphthyl, where the said radicals are preferably unsubstituted but can also be substituted once, twice or three times by the said radicals, in particular A, F, Cl, Br, methylenedioxy, COOH, COOCH₃, O—CO—A, COOC₂H₅, CF₃, OH or OA.

Het is preferably 2- or 3-furyl, 2- or 3-thienyl, 1-, 2- or 3-pyrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothioazolyl, 2-, 3- or 4-pyridyl, 2-, 4-, 5- or 6-pyrimidinyl, and further preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzthiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-cinnolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals can also be partially or completely hydrogenated.

Het can thus also be, for example, 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazanyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or 8-isoquinolinyl.

It applies to the invention in its entirety that all radicals which occur more than once can be identical or different, that is to say are independent of one another.

Accordingly, the invention particularly relates to those compounds of the formula I in which at least one of the said radicals has one of the meanings stated above as preferred. Some preferred groups of compounds can be expressed by the following formulae Ia to Ih, which correspond to the formula I and in which the undefined radicals have the meaning stated for formula I, but in which in Ia R is

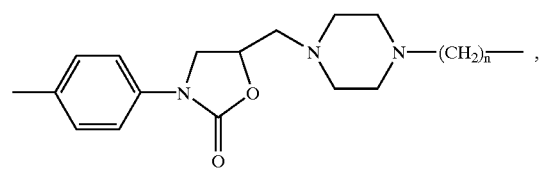

and n is 1 or 2 and R¹ is hydrogen;

in Ib R is

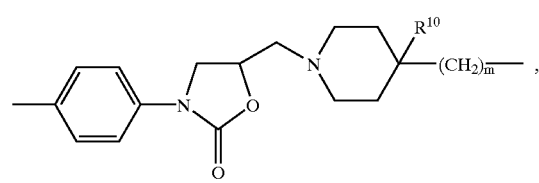

R¹⁰ is hydrogen or OH, m is 0 or 1 and R¹ is hydrogen;

in Ic R is

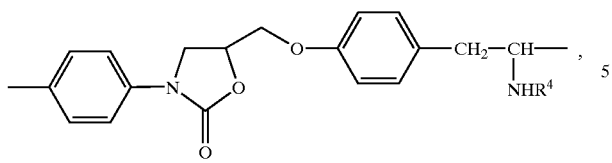

and $R^1$ is hydrogen;
in Id R is

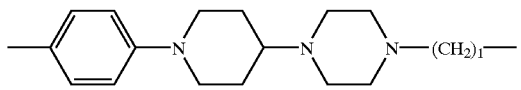

with l=1 or 2, and $R^1$ is hydrogen;
in Ie R is

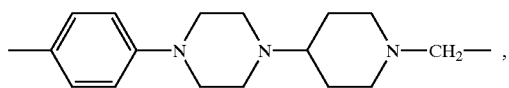

$R^1$ is hydrogen and $R^2$ is OH or OA;
in If R is

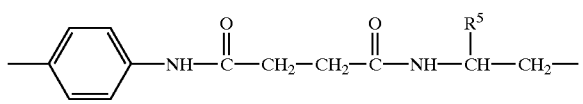

with $R^5$=A, alkenyl or alkynyl with 2–4 C atoms;

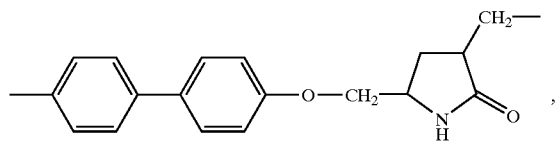

or

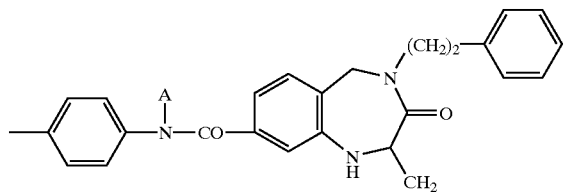

or

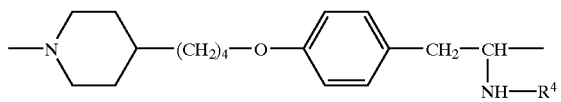

with $R^4$=A—$SO_2$— or Ar—$SO_2$—;

in Ig $R^3$ is benzoyl, 1- or 2-naphthoyl, furoyl, thienoyl or carbobenzoxy and $R^2$ is OH or OA;

in Ih R is

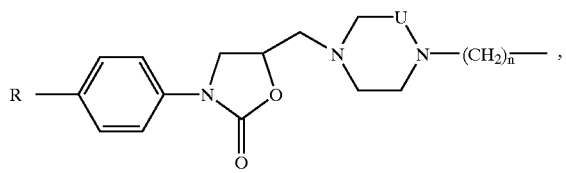

n is 1 or 2, U is CO or $CH_2$, $R^2$ is OH or OA and $R^3$ is benzoyl or 1- or 2-naphthoyl.

The compounds of the formula I as well as the starting materials for preparing them are moreover prepared by methods known per se, as described in the literature (for example in the standard works such as Houben-Weyl, Methoden der organischen Chemie [Methods of organic chemistry], Georg-Thieme-Verlag, Stuttgart; also J. Med. Chem. 37, 3881–3886 (1994), EP-A1-0 381 033, EP-A1-0 462 960), specifically under reaction conditions known and suitable for the said reactions. It is moreover also possible to make use of variants which are known per se but not mentioned here in detail.

The starting materials can, if required, also be formed in situ, so that they are not isolated from the reaction mixture but immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which otherwise correspond to the formula I but contain, in place of one or more free amino and/or hydroxyl groups, corresponding protected amino and/or hydroxyl groups, preferably those which have in place of an H atom which is bonded to an N atom an amino protective group, in particular those which have in place of an HN group an R'—N group in which R' is an amino protective group, and/or those which have in place of the H atom of a hydroxyl group a hydroxyl protective group, for example those which correspond to the formula I but have in place of a —COOH group a —COOR" group in which R" is a hydroxyl protective group.

It is also possible for a plurality of identical or different protected amino and/or hydroxyl groups to be present in the molecule of the starting material. If the protective groups which are present differ from one another, they can in many cases be eliminated selectively.

The term "amino protective group" is generally known and refers to groups which are suitable for protecting (blocking) an amino group from chemical reactions but which can easily be removed after the desired chemical reaction has been carried out elsewhere in the molecule. Typical of such groups are, in particular, unsubstituted or substituted acyl, aryl (for example 2,4-dinitrophenyl (DNP)), aralkoxymethyl (for example benzyloxymethyl (BOM)) or aralkyl groups (for example benzyl, 4-nitrobenzyl, triphenylmethyl). Since the amino protective groups are removed after the desired reaction (or sequence of reactions), their nature and size is moreover not critical; however, those with 1–20, in particular 1–8, C atoms are preferred. The term "acyl group" in connection with the present process is to be interpreted in the widest sense. It embraces acyl groups derived from aliphatic, araliphatic, aromatic or heterocyclic carboxylic acids or sulfonic acids, and, in particular, alkoxycarbonyl, aryloxycarbonyl and, especially, aralkoxycarbonyl groups. Examples of acyl groups of these types are alkanoyls such as acetyl, propionyl, butyryl; aralkanoyls such as phenylacetyl; aroyls such as benzoyl or toluyl; aryloxyalkanoyls such as phenoxyacetyl; alkoxycarbonyls such as methoxycarbonyl, ethoxycarbonyl, 2,2,2-trichloroethoxycarbonyl, isopropoxycarbonyl, tert-butoxycarbonyl (BOC), 2-iodoethoxycarbonyl; aralkyloxycarbonyl such as benzyloxycarbonyl (CBZ), 4-methoxybenzyloxycarbonyl, 9-fluorenylmethoxycarbonyl (FMOC). Preferred amino protective groups are BOC, DNP and BOM, also CBZ, benzyl and acetyl.

The term "hydroxyl protective group" is likewise generally known and refers to groups which are suitable for protecting a hydroxyl group from chemical reactions but which can easily be removed after the desired chemical reaction has been carried out elsewhere in the molecule. Typical of such groups are the abovementioned unsubstituted or substituted aryl, aralkyl or acyl groups, furthermore also alkyl groups. The nature and size of the hydroxyl protective groups is not critical because they are removed again after the desired chemical reaction or sequence of reactions; preferred groups have 1–20, in particular 1–10, C atoms. Examples of hydroxyl protective groups are, inter alia, tert-butyl, benzyl, p-nitrobenzoyl, p-toluenesulfonyl and acetyl, with benzyl and acetyl being particularly preferred.

The functional derivatives of the compounds of the formula I which are to be used as starting materials can be prepared by conventional methods as described, for example, in the stated standard works and patents, for example by reacting compounds which correspond to the formula II and III but where at least one of these compounds contains a protective group in place of an H atom.

The liberation of the compounds of the formula I from their functional derivatives takes place, depending on the protective group used, for example with strong acids, preferably with trifluoroacetic acid. or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible but not always necessary.

Suitable and preferred inert solvents are organic, for example carboxylic acids such as acetic acid, ethers such as tetrahydrofuran or dioxane, amides such as dimethylformamide (DMF), halogenated hydrocarbons such as dichloromethane, sulfoxides such as dimethyl sulfoxide (DMSO), furthermore also alcohols such as methanol, ethanol or isopropanol, and water. Mixtures of the abovementioned solvents are also suitable.

Trifluoroacetic acid is preferably used in excess without addition of another solvent, perchloric acid in the form of a mixture of acetic acid and 70% perchloric acid in the ratio 9:1. The reaction temperatures for the cleavage are preferably from about 0 to about 50° C., preferably from 15 to 30° C. (room temperature).

The BOC group can be eliminated, for example, preferably with 40 trifluoroacetic acid in dichloromethane or with about 3 to 5 N HCl in dioxane at 15–60° C., and the FMOC group with an approximately 5–20% solution of dimethylamine, diethylamine or piperidine in DMF at 15–50°. The DNP group is eliminated, for example, also with an approximately 3–10% solution of 2-mercaptoethanol in DMF/water at 15–30°.

Protective groups which can be eliminated by hydrogenolysis (for example BOM, CBZ or benzyl) can be eliminated, for example, by treatment with hydrogen in the presence of a catalyst (for example of a noble metal catalyst such as palladium, preferably on a support such as carbon). Suitable solvents in this case are those mentioned above, especially, for example, alcohols such as methanol or ethanol or amides such as DMF. The hydrogenolysis is, for example, carried out at temperatures from about 0 to 100° C. and at pressures from about 1 to 200 bar, preferably 20–3.0° C. and 1–10 bar. Hydrogenolysis of the CBZ group takes place satisfactorily, for example, on 5–10% Pd—C in methanol at 20–30° C.

Compounds of the formula I can preferably also be obtained by reacting a compound of the formula II with a carboxylic acid derivative of the formula III. In this case the known methods for the acylation of amines are preferably used.

The group X in the formula III is preferably Cl, Br, I, $C_1$-$C_6$-alkylsulfonyloxy such as methane- or ethanesulfonyloxy or $C_6 C_{10}$-arylsulfonyloxy such as benzene-, p-toluene- or 1- or 2-naphthalenesulfonyloxy.

The reaction preferably takes place in the presence of an additional base, for example of an alkali metal or alkaline earth metal hydroxide or carbonate such as sodium, potassium or calcium hydroxide, sodium, potassium or calcium carbonate, in an inert solvent, for example a halogenated hydrocarbon such as dichloromethane, an ether such as THF or dioxane, an amide such as DMF or dimethylacetamide, a nitrile such as acetonitrile, at temperatures from about −10 to 200° C., preferably from 0 to 120° C. If the leaving group is different from iodine, it is advisable to add an iodide such as potassium iodide.

The starting materials of the formula II are, generally, known and can be prepared, for example, by the methods described in EP 0 623 615 (corresponding to DE 43 14 378).

To prepare an amidine of the formula II, ammonia can be added onto a nitrile of the formula II. The addition preferably takes place in several stages by, in a manner known per se, a) converting the nitrile with $H_2S$ into a thioamide which is converted with an alkylating agent, for example $CH_3I$, into the corresponding S-alkylimidothioester which in turn reacts with $NH_3$ to give the amidine, b) converting the nitrile with an alcohol, for example ethanol, in the presence of HCl into the corresponding imidoester and treating the latter with ammonia, or c) reacting the nitrile with lithium bis(trimethylsilyl)amide and subsequently hydrolyzing the product.

The corresponding N-hydroxyamidines of the formula II can be obtained analogously from the nitrites when hydroxylamine is used in place of ammonia in a) or b). These products can then also be modified by, for example, reducing them with hydrogen gas.

The compounds of the formula III are known and most of them are commercially available.

Reaction of compounds II with compounds III takes place as already described previously.

It is furthermore possible to obtain a compound of the formula I in which R is (a), (b), (c) or (d) by reacting a compound of the formula IV with a compound of the formula Va or Vb.

Some of the compounds of the formula IV are disclosed in EP 0 623 615, or they can be prepared by the methods described therein.

They can be prepared, for example, by reacting a substituted aniline of the formula R*—$NH_2$ with a compound of the formula $R^5CH_2$—$CHR^6$—$CH_2OH$ (in which $R^5$ is Cl, Br or another suitable leaving group, and $R^6$ is OH or $R^5$ and $R^6$ together are also O) to give a compound of the formula R*—NH—$CH_2$—$CHR^8$—$CH_2OH$ (in which $R^8$ is OH), reacting with a derivative of carbonic acid such as diethyl carbonate to give 3-R*-5-hydroxymethyl-2-oxazolidinones and, where- appropriate, converting the hydroxymethyl group into a CH$_2$Z' group (where Z is a leaving group), for example with SOCl$_2$, SOBr$_2$, methanesulfonyl chloride or p-toluenesulfonyl chloride. The compounds of the formula Vb are, generally, known or can be prepared in analogy to known compounds from suitable phenol derivatives or from phenol. The same applies to compounds of the formula Va. They can be prepared by methods known per se from piperidine or piperazine derivatives.

The reaction takes place under similar conditions as previously described for the reaction between compounds II and III.

Compounds of the formula I can furthermore be obtained by reacting a compound of the formula IV (or a reactive derivative thereof) with a reactive derivative of carbonic acid.

Particularly suitable carbonic acid derivatives are dialkyl carbonates such as diethyl carbonate, furthermore also alkyl chloroformates such as ethyl chloroformate. The carbonic acid derivative is preferably used in excess and preferably also serves as solvent or suspending agent.

However, it is also possible for one of the stated solvents to be present as long as it is inert in this reaction. It is furthermore advisable to add a base, in particular an alkali metal alcoholate such as potassium tert-butoxide. The reaction is preferably carried out at temperatures from 0 to 150° C., preferably from 70 to 120° C.

The starting materials of the formula IV are, as a rule, novel. They can be obtained, for example, by functionalization of the abovementioned compounds of the formula R*—NH—CH$_2$—CH(OH)—CH$_2$OH to give compounds of the formula R*—NH—CH$_2$—CH(OH)—CH$_2$—Z and reaction with compounds of the formula Va or Vb.

It is likewise possible to obtain compounds of the formula I in which

is (e), (f), (g), (h), (i) or (k) by reacting a compound of the formula VII with a compound of the formula VIII.

The preparation of compounds VII and VIII can take place by methods known per se as described, for example, in J. March, Adv. Org. Chem. 3rd Edition, J. Wiley & Sons (1985).

Thus, for example, it is possible to prepare a compound of the formula VII by converting a p-CN-aniline which is, where appropriate, derivatized on the NH$_2$ group, as previously described, into a p-amidinoaniline and subsequently to acylate the latter with a compound of the formula R$^3$—X where X is preferably Cl or Br. It is furthermore possible for a benzoic acid derivative which is substituted by the radical R$^3$—NH—C(=NR$^1$) to be converted into another acid derivative or be linked to an amino acid or an appropriately derivatized amino acid in order to obtain a compound of the formula VII.

The preparation of the carboxylic acids or carboxylic acid derivatives of the formula VIII is trivial and can take place by methods known per se.

The reaction of VII with VIII is likewise preferably carried out in the presence of a base or with an excess of the basic component. Suitable and preferred bases are, for example, alkali metal or alkaline earth metal hydroxides, carbonates, alcoholates or organic bases such as triethylamine or pyridine, which can also be used in excess and then may simultaneously serve as solvents.

Particularly suitable inert solvents are alcohols such as methanol, ethanol, or isopropanol, n-butanol or tert-butanol; ethers such as diethyl ether, diisopropyl ether, THF or dioxane; glycol ethers such as ethylene glycol monomethyl or monoethyl ether (methyl glycol or ethyl glycol), ethylene glycol dimethyl ether (diglyme); ketones such as acetone or butanone; nitriles such as acetonitrile; nitro compounds such as nitromethane or nitrobenzene; esters such as ethyl acetate; amides such as hexamethylphosphoric triamide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Mixtures of these solvents with one another are also suitable.

Preferred reaction temperatures are between room temperature and the boiling point of the solvent chosen.

Compounds of the formula I can also be prepared by reacting a compound of the formula IX with a compound of the formula X.

Concerning the preparation of the precursors IX and X, and the reaction of the two compounds with one another, what has already been said above for the compounds VII and VIII applies.

It is furthermore possible to convert a radical R$^2$ in a compound of the formula I into another radical R$^2$ by hydrolyzing an ester of the formula I or esterifying a carboxylic acid of the formula I.

For esterification, an acid of the formula I (R$^2$=H) can be treated with an excess of an alcohol of the formula R$^2$—OH (R$^2$=A or benzyl), preferably in the presence of a strong acid such as hydrochloric acid or sulfuric acid at temperatures from 0 to 100° C., preferably 20 to 50° C.

Conversely, an ester of the formula I (R$^2$=A or benzyl) can be converted into the corresponding acid of the formula I (R$^2$=H), preferably by solvolysis or hydrogenolysis by one of the methods stated above, for example with NaOH or KOH in water/dioxane at temperatures from 0 to 40° C., preferably 10 to 30° C.

It is likewise possible for cyano groups to be completely or partially hydrolyzed.

It is furthermore possible to convert one radical R$^1$ and/or R$^3$ into another radical R$^1$ and/or R$^3$.

In particular, primary or secondary amino groups can be alkylated, acylated, amidinated or provided with conventional amino protective groups or alkyl- or arylsulfonyl groups or, conversely, be liberated by removing these groups.

A base of the formula I can be converted with an acid into the relevant acid addition salt. Particularly suitable acids for this reaction are those which afford physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, sulfamic acid, furthermore organic acids, especially aliphatic, alicyclic, araliphatic, aromatic or heterocyclic mono- or polybasic carboxylic, sulfonic or sulfuric acids, for example formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulphonic acids, lauryl sulfuric acid. Salts with physiologically unacceptable acids, for example picrates, can be used to isolate and/or purify the compounds of the formula I.

The free bases of the formula I can, if required, be liberated from their salts by treatment with strong bases such as sodium or potassium hydroxide, sodium or potassium carbonate.

It is also possible to convert carboxylic acids of the formula I ($R^2$=H) by reaction with appropriate bases into their metal or ammonium salts, for example their sodium, potassium or calcium salts.

The compounds of the formula I contain one or more chiral centers and may therefore exist in racemic or optically active form. Racemates which are obtained can be separated by methods known per se, mechanically or chemically, into the enantiomers. Diastereomers are preferably formed from the racemic mixture by reaction with an optically active resolving agent. Examples of suitable resolving agents are optically active acids such as the D and L forms of tartaric acid, diacetyltartaric acid, dibenzoyltartaric acid, mandelic acid, malic acid, lactic acid or the various optically active camphorsulfonic acids such as β-camphorsulfonic acid. It is also advantageous to separate enantiomers using a column packed with an optically active resolving agent (for example dinitrobenzoyl-phenylglycine); suitable as mobile phase is, for example, a hexane/isopropanol/acetonitrile mixture, for example in the ratio 82:15:3 by volume.

It is, of course, also possible to obtain optically active compounds of the formula I in the methods described above by using starting materials (for example those of the formula II) which are already optically active.

The compounds of the formula I may likewise occur in tautomeric forms. The invention includes all these tautomers.

The novel compounds of the formula I and their physiologically acceptable salts can be used to produce pharmaceutical products by converting them, together with at least one vehicle or ancillary substance and, if required, together with one or more other active substance(s), into a suitable dosage form. The formulations obtained in this way can be used as pharmaceuticals in human or veterinary medicine. Suitable carrier substances are organic or inorganic substances which are suitable for enteral (for example oral or rectal) or parenteral administration or for administration in the form of an inhalation spray and which do not react with the novel compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc, cellulose. Used for oral administration are, in particular, tablets, coated tablets, capsules, syrups, solutions or drops; specifically of interest are lacquered tablets and capsules with coatings or capsule shells which are resistant to gastric fluid. Used for rectal administration are suppositories, and for parenteral administration are solutions, preferably oily or aqueous solutions, furthermore suspensions, emulsions or implants.

For administration as inhalation sprays it is possible to use sprays which contain the active substance either dissolved or suspended in a propellant gas mixture. In this case, the active substance is preferably used in micronized form, it being possible for one or more additional physiologically tolerated solvents to be present, for example ethanol. Inhalation solutions can be administered with the aid of conventional inhalers. The novel compounds can also be lyophilized, and the resulting lyophilizates can be used, for example, to produce injectable products. The stated formulations can be sterilized and/or contain ancillary substances such as preservatives, stabilizers and/or wetting agents, emulsifiers, salts to influence the osmotic pressure, buffer substances, colorants and/or flavorings. They can, if required, also contain one or more other active substances, for example one or more vitamins.

The substances according to the invention are, for example, administered in analogy to other known drugs which are commercially available, but especially in analogy to the compounds described in EP-A-459 256, preferably in doses from about 5 mg to 1 g, in particular from 50 to 500 mg, per dosage unit. The daily dosage is preferably from about 0.1 to 20 mg/kg, in particular 1 to 10 mg/kg, of body weight. The specific dose for each particular patient depends, however, on a wide variety of factors, for example on the activity of the specific compound used, on the age, body weight, general state of health, sex, on the diet, on the time and route of administration, on the rate of excretion, medicinal substance combination and severity of the particular disorder for which the therapy is applied. Oral administration is preferred.

Hereinbefore and hereinafter, all temperatures are stated in ° C. In the following examples, "usual working up" means: if required, water is added, the pH is adjusted to between 2 and 8, depending on the nature of the final product, filtration through an ion exchange column is carried out, the organic phase is dried over sodium sulfate, evaporated, lyophilized where appropriate and purified by chromatography on silica gel and/or crystallization. In the following examples, "4-piperidylethyl" always means "2-(4-piperidyl)ethyl," "4-piperidylpropyl" always means "3-(4-piperidyl) propyl" and "4-piperidylbutyl" always means "4-(4-piperidyl)butyl." Likewise, "4-piperazinylethyl" always means "2-(4-piperazinyl) ethyl," "4-piperazinylpropyl" means "3-(4-piperazinyl)propyl" and "4-piperazinylbutyl" means "4-(4-piperazinyl)butyl." These also include the derivatives provided with protective groups, for example the BOC-protected compounds.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, unless otherwise indicated, all parts and percentages are by weight.

The entire disclosure of all applications, patents and publications, cited above and below, and of corresponding German application 195 16 483.0, filed May 5, 1995, are hereby incorporated by reference.

EXAMPLES

Example 1

3.0 g of 3-[4-(N-benzoylamidino)phenyl]-5-methanesulfonyloxymethyl-2-oxazolidinone [obtainable by reacting 4-(5-oxo-1,2,4-oxadiazolin-3-yl)aniline with 2,3-epoxypropan-1-ol to give N-[4-(5-oxo-1,2,4-oxadiazolin-3-yl)phenyl]-2,3-dihydroxypropylamine, reacting with diethyl carbonate in the presence of tert-butoxide to give 3-[4-(5-oxo-1,2,4-oxazolin-3-yl)phenyl]-5-hydroxymethyl-2-oxazolidinone, reductive cleavage of the 5-oxo-1,2,4-oxadiazoline group, reacting with benzoyl chloride and subsequently esterifying with methanesulfonyl chloride) dissolved in 10 ml of DMF, are added to a solution of 1.2 g of 4-ethoxycarbonylmethylpiperazine ("A") in 20 ml of DMF, and the mixture is stirred at room temperature for 60 min. Removal of the solvent and the usual working up result in 3-[4-(N-benzoylamidino)phenyl]-5-(4-ethoxycarbonylmethylpiperazinomethyl)-2-oxazolidinone, m.p. 114°.

The following are obtained analogously by reacting "A" with 3-[4-(N-benzoylamidino)phenyl]-5(R)-methanesulfonyloxymethyl-2-oxazolidinone 3-[4-(N-benzoylamidino)phenyl]-5(R)-(4-ethoxycarbonylmethylpiperazinomethyl)-2-oxazolidinone, m.p. 150°;

with 3-[4-(N-benzyloxycarbonylamidino)phenyl]-5-methanesulfonyloxymethyl-2-oxazolidinone 3-[4-(N-benzyloxycarbonylamidino)phenyl]-5-(4-ethoxycarbonylmethylpiperazinomethyl)-2-oxazolidinone, m.p. 129°;

with 3-[4-(N-phenoxycarbonylamidino)phenyl]-5-methanesulfonyloxymethyl-2-oxazolidinone 3-[4-(N-phenoxycarbonylamidino)phenyl]-5-(4-ethoxycarbonylmethylpiperazinomethyl)-2-oxazolidinone, m.p. 176°;

with 3-[4-(N-(3-pyridylcarbonyl)-amidino)-phenyl]-5-methanesulfonyloxymethyl-2-oxazolidinone 3-[4-(N-(3-pyridylcarbonyl)-amidino)-phenyl]-5-(4-ethoxycarbonylmethylpiperazinomethyl)-2-oxazolidinone, m.p. 134–135°;

with 3-[4-(N-(1-methyl-4-piperidyloxycarbonyl)-amidino) phenyl]-5-methanesulfonyloxymethyl-2-oxazolidinone 3-[4-(N-(1-methyl-4-piperidyloxycarbonyl)-amidino) phenyl]-5-(4-ethoxycarbonylmethyl-piperazinomethyl)-2-oxazolidinone, dihydrochloride, m.p. 91–93°;

with 3-[4-(N-1-naphthoylamidino)phenyl]-5-methanesulfonyloxymethyl-2-oxazolidinone 3-[4-(N-1-naphthoylamidino)phenyl]-5-(4-ethoxycarbonylmethylpiperazinomethyl)-2-oxazolidinone, m.p. 160–161°;

with 3-[4-(N-2-naphthoylamidino)phenyl]-5-methanesulfonyloxymethyl-2-oxazolidinone 3-[4-(N-2-naphthoylamidino)phenyl]-5-(4-ethoxycarbonylmethylpiperazinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5(4-ethoxycarbonylmethylpiperazinomethyl)-2-oxazolidinone, m.p. 172–173°;

with 3-[4-(N-3-furoylamidino)phenyl]-5-methanesulfonyloxymethyl-2-oxazolidinone 3-[4-(N-3-furoylamidino)phenyl]-5-(4-ethoxycarbonylmethylpiperazinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(4-ethoxycarbonylmethylpiperazinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(4-ethoxycarbonylmethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-ethoxycarbonylmethylpiperazinomethyl)-2-oxazolidinone, 186–187°.

Example 2

In analogy to Example 1, 3-[4-(N-benzoylamidino) phenyl]-5-(4-ethoxycarbonylethyl-piperazinomethyl)-2-oxazolidinone, m.p. 163–164°, is obtained by reacting 1.2 g of 4-ethoxycarbonylethylpiperazine ("B") in 20 ml of DMF with 3.0 g of 3-[4-(N-benzoylamidino)phenyl]-5-methanesulfonyloxymethyl-2-oxazolidinone [obtainable as described in Example 1], dissolved in 10 ml of DMF, after removal of the solvent and the usual working up.

The following are obtained analogously by reacting "B" with 3-[4-(N-benzoylamidino)phenyl]-5(S)-methanesulfonyloxymethyl-2-oxazolidinone 3-[4-(N-benzoylamidino)phenyl]-5(S)-(4-ethoxycarbonylethylpiperazinomethyl)-2-oxazolidinone, m.p. 149–150°; $[\alpha]^D_{20}$=−32,6° (DMSO);

with 3-[4-(N-benzoylamidino)phenyl]-5(R)-methanesulfonyloxymethyl-2-oxazolidinone 3-[4-(N-benzoylamidino)phenyl]-5(R)-(4-ethoxycarbonylethylpiperazinomethyl)-2-oxazolidinone; m.p. 225–226°; $[\alpha]^D_{20}$=+33,0° (DMSO);

with 3-[4-(N-benzyloxycarbonylamidino)phenyl]-5-methanesulfonyloxymethyl-2-oxazolidinone 3-[4-(N-benzyloxycarbonylamidino)phenyl]-5-(4-ethoxycarbonylethylpiperazinomethyl)-2-oxazolidinone, m.p. 130–131°;

with 3-[4-(N-benzyloxycarbonylamidino)phenyl]-5R-methanesulfonyloxymethyl-2-oxazolidinone 3-[4-(N-benzyloxycarbonylamidino)phenyl]-5R-(4-ethoxycarbonylethylpiperazinomethyl)-2-oxazolidinone, m.p. 133–134°, $[\alpha]^D_{20}$=+29,5° (DMSO);

with 3-[4-(N-phenoxycarbonylamidino)phenyl]-5-methanesulfonyloxymethyl-2-oxazolidinone 3-[4-(N-phenoxycarbonylamidino)phenyl]-5-(4-ethoxycarbonylethylpiperazinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5-(4-ethoxycarbonylethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-ethoxycarbonylethylpiperazinomethyl)-2-oxazolidinone, m.p. 168°;

with 3-[4-(N-(1-methyl-4-piperidyloxycarbonyl)-amidino) phenyl]-5-methanesulfonyloxymethyl-2-oxazolidinone 3-[4-(N-(1-methyl-4-piperidyloxycarbonyl)amidino) phenyl]-5-(4-ethoxycarbonylethylpiperazinomethyl)-2-oxazolidinone;

with 3-[4-(N-ethoxycarbonylmethylcarbamoylamidino) phenyl]-5-methanesulfonyloxymethyl-2-oxazolidinone 3-[4-(N-ethoxycarbonylmethylcarbamoylamidino) phenyl]-5-(4-ethoxycarbonylethylpiperazinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(4-ethoxycarbonylethylpiperazinomethyl)-2-oxazolidinone;

with 3-[4-(N-1-naphthoylamidino)phenyl]-5-methanesulfonyloxymethyl-2-oxazolidinone 3-[4-(N-1-naphthoylamidino)phenyl]-5-(4-ethoxycarbonylethylpiperazinomethyl)-2-oxazolidinone;

with 3-[4-(N-2-naphthoylamidino)phenyl]-5-methanesulfonyloxymethyl-2-oxazolidinone 3-[4-(N-2-naphthoylamidino)phenyl]-5-(4-ethoxycarbonylethylpiperazinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(4-ethoxycarbonylethylpiperazinomethyl)-2-oxazolidinone;

with 3-[4-(N-3-furorylamidino)phenyl]-5-methanesulfonyloxymethyl-2-oxazolidinone 3-[4-(N-3- furoylamidino)phenyl]-5-(4-ethoxycarbonylethylpiperazinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(4-ethoxycarbonylethylpiperazinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(4-ethoxycarbonylethylpiperazinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(4-ethoxycarbonylethylpiperazinomethyl)-2-oxazolidinone.

Example 3

In analogy to Example 1, 3-[4-(N-benzoylamidino)phenyl-5-(4-tert-butoxycarbonylethyl-piperazinomethyl)-2-oxazolidinone, m.p. 136–137°, is obtained starting from 1.2 g of 4-tert-butoxycarbonylethylpiperazine ("C") in 20 ml of DMF by reaction with 3.0 g of 3-[4-(N-benzoylamidino)phenyl]-5-methanesulfonyloxymethyl-2-oxazolidinone [obtainable as described in Example 1] after removal of the solvent and the usual working up.

The following are obtained analogously by reacting "C"

with 3-[4-(N-benzyloxycarbonylamidino)phenyl]-5-methanesulfonyloxymethyl-2-oxazolidinone 3-[4-(N-benzyloxycarbonylamidino)phenyl]-5-(4-tert-butoxycarbonylethylpiperazinomethyl)-2-oxazolidinone, m.p. 133°;

with 3-[4-(N-phenoxycarbonylamidino)phenyl]-5-methanesulfonyloxymethyl-2-oxazolidinone 3-[4-(N-phenoxycarbonylamidino)phenyl]-5-(4-tert-butoxycarbonylethylpiperazinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5-(4-tert-butoxycarbonylethylpiperazinomethyl)-2-oxazolidinone;

with 3-[4-(N-(1-methyl-4-piperidyloxycarbonyl)amidino)phenyl]-5-methanesulfonyloxymethyl-2-oxazolidinone 3-[4-(N-(1-methyl-4-piperidyloxycarbonyl)amidino)phenyl]-5-(4-tert-butoxycarbonylethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-tert-butoxycarbonylethylpiperazinomethyl)-2-oxazolidinone, m.p. 174°;

with 3-[4-(N-ethoxycarbonylmethylcarbamoylamidino)phenyl]-5-methanesulfonyloxymethyl-2-oxazolidinone 3-[4-(N-ethoxycarbonylmethylcarbamoylamidino)phenyl]-5-(4-tert-butoxycarbonylethylpiperazinomethyl)-2-oxazolidinone, m.p. 80°;

with 3-[4-(N-methylsulfonylamidino)phenyl]-5-methanesulfonyloxymethyl-2-oxazolidinone 3-[4-(N-methylsulfonylamidino)phenyl]-5-(4-tert-butoxycarbonylethylpiperazinomethyl)-2-oxazolidinone, m.p. 205°;

with 3-[4-(N-1-naphthoylamidino)phenyl]-5-methanesulfonyloxymethyl-2-oxazolidinone 3-[4-(N-1-naphthoylamidino)phenyl]-5-(4-tert-butoxycarbonylethylpiperazinomethyl)-2-oxazolidinone, m.p. 111–113°;

with 3-[4-(N-2-naphthoylamidino)phenyl]-5-methanesulfonyloxymethyl-2-oxazolidinone 3-[4-(N-2-naphthoylamidino)phenyl]-5-(4-tert-butoxycarbonylethylpiperazinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(4-tert-butoxycarbonylethylpiperazinomethyl)-2-oxazolidinone.

Example 4

In analogy to Example 1, the following are obtained starting from 4-methoxycarbonylethylpiperazine by reacting with 3-[4-(N-benzyloxycarbonylamidino)phenyl]-5-methanesulfonyloxymethyl-2-oxazolidinone 3-[4-(N-benzyloxycarbonylamidino)phenyl]-5-(4-methoxycarbonylethylpiperazinomethyl)-2-oxazolidinone;

with 3-[4-(N-benzoylamidino]phenyl]-5-methanesulfonyloxymethyl-2-oxazolidinone 3-[4-(N-benzoylamidino)phenyl]-5-(4-methoxycarbonylethylpiperazinomethyl)-2-oxazolidinone;

with 3-[4-(N-phenoxycarbonylamidinolphenyl]-5-methanesulfonyloxymethyl-2-oxazolidinone 3-[4-(N-phenoxycarbonylamidino)phenyl]-5-(4-methoxycarbonylethylpiperazinomethyl)-2-oxazolidinone;

with 3-[4-(N-(3-pyridylcarbonyl)amidino]phenyl]-5-methanesulfonyloxymethyl-2-oxazolidinone 3-[4-(N-(3-pyridylcarbonylamidino)phenyl]-5-(4-methoxycarbonylethylpiperazinomethyl)-2-oxazolidinone;

with 3-[4-(N-(1-methyl-4-piperidyloxycarbonyl)amidino]phenyl]-5-methanesulfonyloxymethyl-2-oxazolidinone 3-[4-(N-(1-methyl-4-piperidyloxycarbonyl)amidino)phenyl]-5-(4-methoxycarbonylethylpiperazino-methyl)-2-oxazolidinone;

with 3-[4-(N-methoxycarbonylamidino]phenyl]-5-methanesulfonyloxymethyl-2-oxazolidinone 3-[4-(N-methoxycarbonylamidino)phenyl]-5-(4-methoxycarbonylethylpiperazinomethyl)-2-oxazolidinone;

with 3-[4-(N-ethoxycarbonylmethylcarbamoylamidino]phenyl]-5-methanesulfonyloxymethyl-2-oxazolidinone 3-[4-(N-ethoxycarbonylmethylcarbamoylamidino)phenyl]-5-(4-methoxycarbonylethylpiperazinomethyl)-2-oxazolidinone;

with 3-[4-(N-methylsulfonylamidino]phenyl]-5-methanesulfonyloxymethyl-2-oxazolidinone 3-[4-(N-methylsulfonylamidino)phenyl]-5-(4-methoxycarbonylethylpiperazinomethyl)-2-oxazolidinone;

with 3-[4-(N-1-naphthoylamidino]phenyl]-5-methanesulfonyloxymethyl-2-oxazolidinone 3-[4-(N-1-naphthoylamidino)phenyl]-5-(4-methoxycarbonylethylpiperazinomethyl)-2-oxazolidinone;

with 3-[4-(N-2-naphthoylamidino]phenyl]-5-methanesulfonyloxymethyl-2-oxazolidinone 3-[4-(N-2-naphthoylamidino)phenyl]-5-(4-methoxycarbonylethylpiperazinomethyl)-2-oxazolidinone;

with 3-[4-(N-2-furoylamidino]phenyl]-5-methanesulfonyloxymethyl-2-oxazolidinone 3-[4-(N-2-furoylamidino)phenyl]-5-(4-methoxycarbonylethylpiperazinomethyl)-2-oxazolidinone;

with 3-[4-(N-3-furoylamidino]phenyl]-5-methanesulfonyloxymethyl-2-oxazolidinone 3-[4-(N-3-furoylamidino)phenyl]-5-(4-methoxycarbonylethylpiperazinomethyl)-2-oxazolidinone;

with 3-[4-(N-2-thienoylamidino]phenyl]-5-methanesulfonyloxymethyl-2-oxazolidinone 3-[4-(N-2-thienoylamidino)phenyl]-5-(4-methoxycarbonylethylpiperazinomethyl)-2-oxazolidinone;

with 3-[4-(N-3-thienoylamidino]phenyl]-5-methanesulfonyloxymethyl-2-oxazolidinone 3-[4-(N-3-thienoylamidino)phenyl]-5-(4-methoxycarbonylethylpiperazinomethyl)-2-oxazolidinone;

with 3-[4-(N-diphenylacetylamidino]phenyl]-5-methanesulfonyloxymethyl-2-oxazolidinone 3-[4-(N-diphenylacetylamidino)phenyl]-5-(4-methoxycarbonylethylpiperazinomethyl)-2-oxazolidinone.

Example 5

In analogy to Example 1, the following are obtained starting from 4-isopropoxycarbonylethylpiperazine by reacting with 3-[4-(N-benzyloxycarbonylamidino)phenyl]-5-methanesulfonyloxymethyl-2-oxazolidinone 3-[4-(N-benzyloxycarbonylamidino)phenyl]-5-(4-isopropoxycarbonylethylpiperazinomethyl)-2-oxazolidinone;

with 3-[4-(N-benzoylamidino)phenyl]-5-methanesulfonyloxymethyl-2-oxazolidinone 3-[4-(N-benzoylamidino)phenyl]-5-(4-isopropoxycarbonylethylpiperazinomethyl)-2-oxazolidinone;

with 3-[4-(N-phenoxycarbonylamidino)phenyl]-5-methanesulfonyloxymethyl-2-oxazolidinone 3-[4-(N-phenoxycarbonylamidino)phenyl]-5-(4-isopropoxycarbonylethylpiperazinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5-(4-isopropoxycarbonylethylpiperazinomethyl)-2-oxazolidinone;

with 3-[4-(N-(1-methyl-4-piperidyloxycarbonyl)amidino)phenyl]-5-methanesulfonyloxymethyl-2-oxazolidinone 3-[4-(N-(1-methyl-4-piperidyloxycarbonyl)amidino)phenyl]-5-(4-isopropoxycarbonylethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-isopropoxycarbonylethylpiperazinomethyl)-2-oxazolidinone;

with 3-[4-(N-ethoxycarbonylmethylcarbamoylamidino)phenyl]-5-methanesulfonyloxymethyl-2-oxazolidinone 3-[4-(N-ethoxycarbonylmethylcarbamoylamidino)phenyl]-5-(4-isopropoxycarbonylethylpiperazinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(4-isopropoxycarbonylethylpiperazinomethyl)-2-oxazolidinone;

with 3-[4-(N-1-naphthoylamidino)phenyl]-5-methanesulfonyloxymethyl-2-oxazolidinone 3-[4-(N-1-naphthoylamidino)phenyl]-5(4-isopropoxycarbonylethylpiperazinomethyl)-2-oxazolidinone;

with 3-[4-(N-2-naphthoylamidino)phenyl]-5-methanesulfonyloxymethyl-2-oxazolidinone 3-[4-(N-2-naphthoylamidino)phenyl]-5-(4-isopropoxycarbonylethylpiperazinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(4-isopropoxycarbonylethylpiperazinomethyl)-2-oxazolidinone;

with 3-[4-(N-3-furoylamidino)phenyl]-5-methanesulfonyloxymethyl-2-oxazolidinone 3-[4-(N-3-furoylamidino)phenyl]-5-(4-isopropoxycarbonylethylpiperazinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(4-isopropoxycarbonylethylpiperazinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(4-isopropoxycarbonylethylpiperazinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(4-isopropoxycarbonylethylpiperazinomethyl)-2-oxazolidinone.

Example 6

In analogy to Example 1, the following are obtained starting from 4-n-butoxycarbonylethylpiperazine by reacting with 3-[4-(N-benzyloxycarbonylamidino)phenyl]-5-methanesulfonyloxymethyl-2-oxazolidinone 3-[4-(N-benzyloxycarbonylamidino)phenyl]-5-(4-n-butoxycarbonylethylpiperazinomethyl)-2-oxazolidinone;

with 3-[4-(N-benzoylamidino)phenyl]-5-methanesulfonyloxymethyl-2-oxazolidinone 3-[4-(N-benzoylamidino)phenyl]-5-(4-n-butoxycarbonylethylpiperazinomethyl)-2-oxazolidinone;

with 3-[4-(N-phenoxycarbonylamidino)phenyl]-5-methanesulfonyloxymethyl-2-oxazolidinone 3-[4-(N-phenoxycarbonylamidino)phenyl]-5-(4-n-butoxycarbonylethylpiperazinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5-(4-n-butoxycarbonylethylpiperazinomethyl)-2-oxazolidinone;

with 3-[4-(N-(1-methyl-4-piperidyloxycarbonyl)amidino)phenyl]-5-methanesulfonyloxymethyl-2-oxazolidinone 3-[4-(N-(1-methyl-4-piperidyloxycarbonyl)amidino)phenyl]-5-(4-n-butoxycarbonylethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-n-butoxycarbonylethylpiperazinomethyl)-2-oxazolidinone;

with 3-[4-(N-ethoxycarbonylmethylcarbamoyl-amidino)phenyl]-5-methanesulfonyloxymethyl-2-oxazolidinone -3-[4-(N-ethoxycarbonylmethylcarbamoylamidino)phenyl]-5-(4-n-butoxycarbonylethylpiperazinomethyl)-2-oxazolidinone;

with 3-[4-(N-methylsulfonylamidino)phenyl]-5-methanesulfonyloxymethyl-2-oxazolidinone 3-[4-(N- methylsulfonylamidino)phenyl]-5-(4-n-butoxycarbonylethylpiperazinomethyl)-2-oxazolidinone;
with 3-[4-(N-1-naphthoylamidino)phenyl]-5-methanesulfonyloxymethyl-2-oxazolidinone 3-[4-(N-1-naphthoylamidino)phenyl]-5-(4-n-butoxycarbonylethylpiperazinomethyl)-2-oxazolidinone;
with 3-[4-(N-2-naphthoylamidino)phenyl]-5-methanesulfonyloxymethyl-2-oxazolidinone 3-[4-(N-2-naphthoylamidino)phenyl]-5-(4-n-butoxycarbonylethylpiperazinomethyl)-2-oxazolidinone;
with 3-[4-(N-2-furoylamidino)phenyl]-5-methanesulfonyloxymethyl-2-oxazolidinone 3-[4-(N-2-furoylamidino)phenyl]-5-(4-n-butoxycarbonylethylpiperazinomethyl)-2-oxazolidinone;
with 3-[4-(N-3-furoylamidino)phenyl]-5-methanesulfonyloxymethyl-2-oxazolidinone 3-[4-(N-3-furoylamidino)phenyl]-5-(4-n-butoxycarbonylethylpiperazinomethyl)-2-oxazolidinone;
with 3-[4-(N-2-thienoylamidino)phenyl]-5-methanesulfonyloxymethyl-2-oxazolidinone 3-[4-(N-2-thienoylamidino)phenyl]-5-(4-n-butoxycarbonylethylpiperazinomethyl)-2-oxazolidinone;
with 3-[4-(N-3-thienoylamidino)phenyl]-5-methanesulfonyloxymethyl-2-oxazolidinone 3-[4-(N-3-thienoylamidino)phenyl]-5-(4-n-butoxycarbonylethylpiperazinomethyl)-2-oxazolidinone;
with 3-[4-(N-diphenylacetylamidino)phenyl]-5-methanesulfonyloxymethyl-2-oxazolidinone 3-[4-(N-diphenylacetylamidino)phenyl]-5-(4-n-butoxycarbonylethylpiperazinomethyl)-2-oxazolidinone.

Example 7

In analogy to Example 1, the following are obtained starting from 4-benzyloxycarbonylethylpiperazine by reacting
with 3-[4-(N-benzyloxycarbonylamidino)phenyl]-5-methanesulfonyloxymethyl-2-oxazolidinone 3-[4-(N-benzyloxycarbonylamidino)phenyl]-5-(4-benzyloxycarbonylethylpiperazinomethyl)-2-oxazolidinone;
with 3-[4-(N-benzoylamidino)phenyl]-5-methanesulfonyloxymethyl-2-oxazolidinone 3-[4-(N-benzoylamidino)phenyl]-5-(4-benzyloxycarbonylethylpiperazinomethyl)-2-oxazolidinone;
with 3-[4-(N-phenoxycarbonylamidino)phenyl]-5-methanesulfonyloxymethyl-2-oxazolidinone 3-[4-(N-phenoxycarbonylamidino)phenyl]-5-(4-benzyloxycarbonylethylpiperazinomethyl)-2-oxazolidinone;
with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5-(4-benzyloxycarbonylethylpiperazinomethyl)-2-oxazolidinone;
with 3-[4-(N-(1-methyl-4-piperidyloxycarbonyl)amidino)phenyl]-5-methanesulfonyloxymethyl-2-oxazolidinone 3-[4-(N-(1-methyl-4-piperidyloxycarbonyl)amidino)phenyl]-5-(4-benzyloxycarbonylethylpiperazinomethyl)-2-oxazolidinone;
with 3-[4-(N-methoxycarbonylamidino)phenyl]-5-methanesulfonyloxymethyl-2-oxazolidinone 3-[4-(N-methoxycarbonylamidino)phenyl]-5-(4-benzyloxycarbonylethylpiperazinomethyl)-2-oxazolidinone;
with 3-[4-(N-ethoxycarbonylmethylcarbamoylamidino)phenyl]-5-methanesulfonyloxymethyl-2-oxazolidinone 3-[4-(N-ethoxycarbonylmethylcarbamoylamidino)phenyl]-5-(4-benzyloxycarbonylethylpiperazinomethyl)-2-oxazolidinone;
with 3-[4-(N-methylsulfonylamidino)phenyl]-5-methanesulfonyloxymethyl-2-oxazolidinone 3-[4-(N-methylsulfonylamidino)phenyl]-5-(4-benzyloxycarbonylethylpiperazinomethyl)-2-oxazolidinone;
with 3-[4-(N-1-naphthoylamidino)phenyl]-5-methanesulfonyloxymethyl-2-oxazolidinone 3-[4-(N-1-naphthoylamidino)phenyl]-5-(4-benzyloxycarbonylethylpiperazinomethyl)-2-oxazolidinone;
with 3-[4-(N-2-naphthoylamidino)phenyl]-5-methanesulfonyloxymethyl-2-oxazolidinone 3-[4-(N-2-naphthoylamidino)phenyl]-5-(4-benzyloxycarbonylethylpiperazinomethyl)-2-oxazolidinone;
with 3-[4-(N-2-furoylamidino)phenyl]-5-methanesulfonyloxymethyl-2-oxazolidinone 3-[4-(N-2-furoylamidino)phenyl]-5-(4-benzyloxycarbonylethylpiperazinomethyl)-2-oxazolidinone;
with 3-[4-(N-3-furoylamidino)phenyl]-5-methanesulfonyloxymethyl-2-oxazolidinone 3-[4-(N-3-furoylamidino)phenyl]-5-(4-benzyloxycarbonylethylpiperazinomethyl)-2-oxazolidinone;
with 3-[4-(N-2-thienoylamidino)phenyl]-5-methanesulfonyloxymethyl-2-oxazolidinone 3-[4-(N-2-thienoylamidino)phenyl]-5-(4-benzyloxycarbonylethylpiperazinomethyl)-2-oxazolidinone;
with 3-[4-(N-3-thienoylamidino)phenyl]-5-methanesulfonyloxymethyl-2-oxazolidinone 3-[4-(N-3-thienoylamidino)phenyl]-5-(4-benzyloxycarbonylethylpiperazinomethyl)-2-oxazolidinone;
with 3-[4-(N-diphenylacetylamidino)phenyl]-5-methanesulfonyloxymethyl-2-oxazolidinone 3-[4-(N-diphenylacetylamidino)phenyl]-5-(4-benzyloxycarbonylethylpiperazinomethyl)-2-oxazolidinone.

Example 8

In analogy to Example 1, the following are obtained starting from 4-methoxycarbonylmethylpiperazine by reacting
with 3-[4-(N-benzyloxycarbonylamidino)phenyl]-5-methanesulfonyloxymethyl-2-oxazolidinone 3-[4-(N-benzyloxycarbonylamidino)phenyl]-5-(4-methoxycarbonylmethylpiperazinomethyl)-2-oxazolidinone;
with 3-[4-(N-benzoylamidino)phenyl]-5-methanesulfonyloxymethyl-2-oxazolidinone 3-[4-(N-benzoylamidino)phenyl]-5-(4-methoxycarbonylmethylpiperazinomethyl)-2-oxazolidinone;
with 3-[4-(N-phenoxycarbonylamidino)phenyl]-5-methanesulfonyloxymethyl-2-oxazolidinone 3-[4-(N-phenoxycarbonylamidino)phenyl]-5-(4-methoxycarbonylmethylpiperazinomethyl)-2-oxazolidinone;
with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5(4-methoxycarbonylmethylpiperazinomethyl)-2-oxazolidinone;

with 3-[4-(N-(1-methyl-4-piperidyloxycarbonyl)amidino) phenyl]-5-methanesulfonyloxymethyl-2-oxazolidinone is 3-[4-(N-(1-methyl-4-piperidyloxycarbonyl)amidino) phenyl]-5-(4-methoxycarbonylmethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-methoxycarbonylmethylpiperazinomethyl)-2-oxazolidinone;

with 3-[4-(N-ethoxycarbonylmethylcarbamoylamidino) phenyl]-5-methanesulfonyloxymethyl-2-oxazolidinone 3-[4-(N-ethoxycarbonylmethylcarbamoylamidino) phenyl]-5-(4-methoxycarbonylmethylpiperazinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(4-methoxycarbonylmethylpiperazinomethyl)-2-oxazolidinone;

with 3-[4-(N-1-naphthoylamidino)phenyl]-5-methanesulfonyloxymethyl-2-oxazolidinone 3-[4-(N-1-naphthoylamidino)phenyl]-5-(4-methoxycarbonylmethylpiperazinomethyl)-2-oxazolidinone;

with 3-[4-(N-2-naphthoylamidino)phenyl]-5-methanesulfonyloxymethyl-2-oxazolidinone 3-[4-(N-2-naphthoylamidino)phenyl]-5-(4-methoxycarbonylmethylpiperazinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(4-methoxycarbonylmethylpiperazinomethyl)-2-oxazolidinone;

with 3-[4-(N-3-furoylamidino)phenyl]-5-methanesulfonyloxymethyl-2-oxazolidinone 3-[4-(N-3-furoylamidino)phenyl]-5-(4-methoxycarbonylmethylpiperazinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(4-methoxycarbonylmethylpiperazinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(4-methoxycarbonylmethylpiperazinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(4-methoxycarbonylmethylpiperazinomethyl)-2-oxazolidinone.

Example 9

In analogy to Example 1, the following are obtained starting from 4-isopropoxycarbonylmethylpiperazine by reacting with 3-[4-(N-benzyloxycarbonylamidino)phenyl]-5-methanesulfonyloxymethyl-2-oxazolidinone 3-[4-(N-benzyloxycarbonylamidino)phenyl]-5-(4-isopropoxycarbonylmethylpiperazinomethyl)-2-oxazolidinone;

with 3-[4-(N-benzoylamidino)phenyl]-5-methanesulfonyloxymethyl-2-oxazolidinone 3-[4-(N-benzoylamidino)phenyl]-5-(4-isopropoxycarbonylmethylpiperazinomethyl)-2-oxazolidinone;

with 3-[4-(N-phenoxycarbonylamidino)phenyl]-5-methanesulfonyloxymethyl-2-oxazolidinone 3-[4-(N-phenoxycarbonylamidino)phenyl]-5-(4-isopropoxycarbonylmethylpiperazinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5-(4-isopropoxycarbonylmethylpiperazinomethyl)-2-oxazolidinone;

with 3-[4-(N-(1-methyl-4-piperidyloxycarbonyl)amidino) phenyl]-5-methanesulfonyloxymethyl-2-oxazolidinone 3-[4-(N-(1-methyl-4-piperidyloxycarbonylamidino) phenyl]-5-(4-isopropoxycarbonylmethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-isopropoxycarbonylmethylpiperazinomethyl)-2-oxazolidinone;

with 3-[4-(N-ethoxycarbonylmethylcarbamoylamidino) phenyl]-5-methanesulfonyloxymethyl-2-oxazolidinone 3-[4-(N-ethoxycarbonylmethylcarbamoylamidino) phenyl]-5-(4-isopropoxycarbonylmethylpiperazinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(4-isopropoxycarbonylmethylpiperazinomethyl)-2-oxazolidinone;

with 3-[4-(N-1-naphthoylamidino)phenyl]-5-methanesulfonyloxymethyl-2-oxazolidinone 3-[4-(N-1-naphthoylamidino)phenyl]-5-(4-isopropoxycarbonylmethylpiperazinomethyl)-2-oxazolidinone;

with 3-[4-(N-2-naphthoylamidino)phenyl]-5-methanesulfonyloxymethyl-2-oxazolidinone 3-[4-(N-2-naphthoylamidino)phenyl]-5-(4-isopropoxycarbonylmethylpiperazinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(4-isopropoxycarbonylmethylpiperazinomethyl)-2-oxazolidinone;

with 3-[4-(N-3-fuorylamidino)phenyl]-5-methanesulfonyloxymethyl-2-oxazolidinone 3-[4-(N-3-fuorylamidino)phenyl]-5-(4-isopropoxycarbonylmethylpiperazinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(4-isopropoxycarbonylmethylpiperazinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(4-isopropoxycarbonylmethylpiperazinomethyl)-2-oxazolidinone;

with 3-[4-(N-diphenylacetylamidino)phenyl]-5-methanesulfonyloxymethyl-2-oxazolidinone 3-[4-(N- diphenylacetylamidino)phenyl]-5-(4-isopropoxycarbonylmethylpiperazinomethyl)-2-oxazolidinone.

Example 10

In analogy to Example 1, the following are obtained starting from 4-n-butoxycarbonylmethylpiperazine by reacting with 3-[4-(N-benzyloxycarbonylamidino)phenyl]-5-methanesulfonyloxymethyl-2-oxazolidinone 3-[4-(N-benzyloxycarbonylamidino)phenyl]-5-(4-n-butoxycarbonylmethylpiperazinomethyl)-2-oxazolidinone;

with 3-[4-(N-benzoylamidino)phenyl]-5-methanesulfonyloxymethyl-2-oxazolidinone 3-[4-(N-benzoylamidino)phenyl]-5-(4-n-butoxycarbonylmethylpiperazinomethyl)-2-oxazolidinone;

with 3-[4-(N-phenoxycarbonylamidino)phenyl]-5-methanesulfonyloxymethyl-2-oxazolidinone 3-[4-(N-phenoxycarbonylamidino)phenyl]-5-(4-n-butoxycarbonylmethylpiperazinomethyl)-2-oxazolidinone;

with 3-[4-(N-(3-pyridylcarbonylamidino)phenyl]-5-methanesulfonyloxymethyl-2-oxazolidinone 3-[4-(N-(3-pyridylcarbonylamidino)phenyl]-5-(4-n-butoxycarbonylmethylpiperazinomethyl)-2-oxazolidinone;

with 3-[4-(N-(1-methylpiperidyl-4-oxycarbonyl)amidino)phenyl]-5-methanesulfonyloxymethyl-2-oxazolidinone; 3-[4-(N-(1-methylpiperidyl-4-oxycarbonyl)amidino)phenyl]-5-(4-n-butoxycarbonylmethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-n-butoxycarbonylmethylpiperazinomethyl)-2-oxazolidinone;

with 3-[4-(N-ethoxycarbonylmethylcarbamoylamidino)phenyl]-5-methanesulfonyloxymethyl-2-oxazolidinone 3-[4-(N-ethoxycarbonylmethylcarbamoylamidino)phenyl]-5-(4-n-butoxycarbonylmethylpiperazinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(4-n-butoxycarbonylmethylpiperazinomethyl)-2-oxazolidinone;

with 3-[4-(N-1-naphthoylamidino)phenyl]-5-methanesulfonyloxymethyl-2-oxazolidinone 3-[4-(N-1-naphthoylamidino)phenyl]-5-(4-n-butoxycarbonylmethylpiperazinomethyl)-2-oxazolidinone;

with 3-[4-(N-2-naphthoylamidino)phenyl]-5-methanesulfonyloxymethyl-2-oxazolidinone 3-[4-(N-2-naphthoylamidino)phenyl]-5-(4-n-butoxycarbonylmethylpiperazinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(4-n-butoxycarbonylmethylpiperazinomethyl)-2-oxazolidinone;

with 3-[4-(N-3-furoylamidino)phenyl]-5-methanesulfonyloxymethyl-2-oxazolidinone 3-[4-(N-3-furoylamidino)phenyl]-5-(4-n-butoxycarbonylmethylpiperazinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(4-n-butoxycarbonylmethylpiperazinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(4-n-butoxycarbonylmethylpiperazinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(4-n-butoxycarbonylmethylpiperazinomethyl)-2-oxazolidinone.

Example 11

In analogy to Example 1, the following are obtained starting from 4-benzyloxycarbonylmethylpiperazine by reacting with 3-[4-(N-benzyloxycarbonylamidino)phenyl]-5-methanesulfonyloxymethyl-2-oxazolidinone 3-[4-(N-benzyloxycarbonylamidino)phenyl]-5-(4-benzyloxycarbonylmethylpiperazinomethyl)-2-oxazolidinone;

with 3-[4-(N-benzoylamidino)phenyl]-5-methanesulfonyloxymethyl-2-oxazolidinone 3-[4-(N-benzoylamidino)phenyl]-5-(4-benzyloxycarbonylmethylpiperazinomethyl)-2-oxazolidinone;

with 3-[4-(N-phenoxycarbonylamidino)phenyl]-5-methanesulfonyloxymethyl-2-oxazolidinone 3-[4-(N-phenoxycarbonylamidino)phenyl]-5-(4-benzyloxycarbonylmethylpiperazinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl) amidino)phenyl]5-(4-benzyloxycarbonylmethylpiperazinomethyl)-2-oxazolidinone;

with 3-[4-(N-(1-methylpiperidyl-4-oxycarbonyl)amidino)phenyl]-5-methanesulfonyloxymethyl-2-oxazolidinone 3-[4-(N-(1-methylpiperidyl-4-oxycarbonylamidino)phenyl]-5-(4-benzyloxycarbonylmethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-benzyloxycarbonylmethylpiperazinomethyl)-2-oxazolidinone;

with 3-[4-(N-ethoxycarbonylmethylcarbamoylamidino)phenyl]-5-methanesulfonyloxymethyl-2-oxazolidinone 3-[4-(N-ethoxycarbonylmethylcarbamoylamidino)phenyl]-5-(4-benzyloxycarbonylmethylpiperazinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(4-benzyloxycarbonylmethylpiperazinomethyl)-2-oxazolidinone;

with 3-[4-(N-1-naphthoylamidino)phenyl]-5-methanesulfonyloxymethyl-2-oxazolidinone 3-[4-(N-1-naphthoylamidino)phenyl]-5-(4-benzyloxycarbonylmethylpiperazinomethyl)-2-oxazolidinone;

with 3-[4-(N-2-naphthoylamidino)phenyl]-5-methanesulfonyloxymethyl-2-oxazolidinone 3-[4-(N-2-naphthoylamidino)phenyl]-5-(4-benzyloxycarbonylmethylpiperazinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(4-benzyloxycarbonylmethylpiperazinomethyl)-2-oxazolidinone;

with 3-[4-(N-3-furoylamidino)phenyl]-5-methanesulfonyloxymethyl-2-oxazolidinone 3-[4-(N-3-furoylamidino)phenyl]-5-(4-benzyloxycarbonylmethylpiperazinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(4-benzyloxycarbonylmethylpiperazinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(4-benzyloxycarbonylmethylpiperazinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(4-benzyloxycarbonylmethylpiperazinomethyl)-2-oxazolidinone.

Example 12

In analogy to Example 1, the following are obtained starting from 3-oxo-4-ethoxycarbonylethylpiperazine by reacting with 3-[4-(N-benzyloxycarbonylamidino)phenyl]-5-methanesulfonyloxymethyl-2-oxazolidinone 3-[4-(N-benzyloxycarbonylamidino)phenyl]-5-(3-oxo-4-ethoxycarbonylethylpiperazinomethyl)-2-oxazolidinone;

with 3-[4-(N-benzoylamidino)phenyl]-5-methanesulfonyloxymethyl-2-oxazolidinone 3-[4-(N-benzoylamidino)phenyl]-5-(3-oxo-4-ethoxycarbonylethylpiperazinomethyl)-2-oxazolidinone, m.p. 164°;

with 3-[4-(N-phenoxycarbonylamidino)phenyl]-5-methanesulfonyloxymethyl-2-oxazolidinone 3-[4-(N-phenoxycarbonylamidino)phenyl]-5-(3-oxo-4-ethoxycarbonylethylpiperazinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5-(3-oxo-4-ethoxycarbonylethylpiperazinomethyl)-2-oxazolidinone;

with 3-[4-(N-(1-methylpiperidyl-4-oxycarbonyl) amidino)phenyl]-5-methanesulfonyloxymethyl-2-oxazolidinone 3-[4-(N-(1-methylpiperidyl-4-oxycarbonyl) amidino)phenyl]-5-(3-oxo-4-ethoxycarbonylethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(3-oxo-4-ethoxycarbonylethylpiperazinomethyl)-2-oxazolidinone;

with 3-[4-(N-ethoxycarbonylmethylcarbamoylamidino) phenyl]-5-methanesulfonyloxymethyl-2-oxazolidinone 3-([4-(N-ethoxycarbonylmethylcarbamoylamidino) phenyl]-5-(3-oxo-4-ethoxycarbonylethylpiperazinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(3-oxo-4-ethoxycarbonylethylpiperazinomethyl)-2-oxazolidinone;

with 3-[4-(N-1-naphthoylamidino)phenyl]-5-methanesulfonyloxymethyl-2-oxazolidinone 3-[4-(N-(1-naphthoylamidino)phenyl]-5-(3-oxo-4-ethoxycarbonylethylpiperazinomethyl)-2-oxazolidinone;

with 3-[4-(N-2-naphthoylamidino)phenyl]-5-methanesulfonyloxymethyl-2-oxazolidinone 3-[4-(N-2-naphthoyl)amidino)phenyl]-5-(3-oxo-4-ethoxycarbonylethylpiperazinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(3-oxo-4-ethoxycarbonylethylpiperazinomethyl)-2-oxazolidinone;

with 3-[4-(N-3-furoylamidino)phenyl]-5-methanesulfonyloxymethyl-2-oxazolidinone 3-[4-(N-3-furoylamidino)phenyl]-5-(3-oxo-4-ethoxycarbonylethylpiperazinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(3-oxo-4-ethoxycarbonylethylpiperazinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(3-oxo-4-ethoxycarbonylethylpiperazinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(3-oxo-4-ethoxycarbonylethylpiperazinomethyl)-2-oxazolidinone.

Example 13

In analogy to Example 1, the following are obtained starting from 3-oxo-4-ethoxycarbonylmethylpiperazine by reacting with 3-[4-(N-benzyloxycarbonylamidino)phenyl]-5-methanesulfonyloxymethyl-2-oxazolidinone 3-[4-(N-benzyloxycarbonylamidino)phenyl]-5-(3-oxo-4-ethoxycarbonylmethylpiperazinomethyl)-2-oxazolidinone;

with 3-[4-(N-benzoylamidino)phenyl]-5-methanesulfonyloxymethyl-2-oxazolidinone 3-[4-(N-benzoylamidino)phenyl]-5-(3-oxo-4-ethoxycarbonylmethylpiperazinomethyl)-2-oxazolidinone, m.p. 180–181° with 3-[4-(N-phenoxycarbonylamidino)phenyl]-5-methanesulfonyloxymethyl-2-oxazolidinone 3-[4-(N-phenoxycarbonylamidino)phenyl]-5-(3-oxo-4-ethoxycarbonylmethylpiperazinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5(3-oxo-4-ethoxycarbonylmethylpiperazinomethyl)-2-oxazolidinone;

with 3-[4-(N-(1-methylpiperidyl-4-oxycarbonyl)amidino) phenyl]-5-methanesulfonyloxymethyl-2-oxazolidinone 3-[4-(N-(1-methylpiperidyl-4-oxycarbonylamidino) phenyl]-5-(3-oxo-4-ethoxycarbonylmethylpiperazinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(3-oxo-4-ethoxycarbonylmethylpiperazinomethyl)-2-oxazolidinone;

with 3-[4-(N-ethoxycarbonylmethylcarbamoylamidino) phenyl]-5-methanesulfonyloxymethyl-2-oxazolidinone 3-[4-(N-ethoxycarbonylmethylcarbamoylamidino) phenyl]-5-(3-oxo-4-ethoxycarbonylmethylpiperazinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(3-oxo-4-ethoxycarbonylmethylpiperazinomethyl)-2-oxazolidinone;

with 3-[4-(N-1-naphthoylamidino)phenyl]-5-methanesulfonyloxymethyl-2-oxazolidinone 3-[4-(N-1-naphthoylamidino)phenyl]-5-(3-oxo-4-ethoxycarbonylmethylpiperazinomethyl)-2-oxazolidinone;

with 3-[4-(N-2-naphthoylamidino)phenyl]-5-methanesulfonyloxymethyl-2-oxazolidinone 3-[4-(N-2-naphthoylamidino)phenyl]-5-(3-oxo-4-ethoxycarbonylmethylpiperazinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(3-oxo-4-ethoxycarbonylmethylpiperazinomethyl)-2-oxazolidinone;

with 3-[4-(N-3-furoylamidino)phenyl]-5-methanesulfonyloxymethyl-2-oxazolidinone 3-[4-(N-3-furoylamidino)phenyl]-5-(3-oxo-4-ethoxycarbonylmethylpiperazinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(3-oxo-4-ethoxycarbonylmethylpiperazinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(3-oxo-4-ethoxycarbonylmethylpiperazinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(3-oxo-4-ethoxycarbonylmethylpiperazinomethyl)-2-oxazolidinone.

Example 14

In analogy to Example 1, the following are obtained starting from 4-ethoxycarbonylpiperidine by reacting with 3-[4-(N-benzyloxycarbonylamidino)phenyl]-5-methanesulfonyloxymethyl-2-oxazolidinone 3-[4-(N-benzyloxycarbonylamidino) phenyl]-5-(4-ethoxycarbonylpiperidinomethyl)-2-oxazolidinone;

with 3-[4-(N-benzoylamidino)phenyl]-5-methanesulfonyloxymethyl-2-oxazolidinone 3-[4-(N-benzoylamidino)phenyl]-5-(4-ethoxycarbonylpiperidinomethyl)-2-oxazolidinone;

with 3-[4-(N-phenoxycarbonylamidino)phenyl]-5-methanesulfonyloxymethyl-2-oxazolidinone 3-[4-(N-phenoxycarbonylamidino)phenyl]-5-(4-ethoxycarbonylpiperidinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5-(4-ethoxycarbonylpiperidinomethyl)-2-oxazolidinone;

with 3-[4-(N-(1-methylpiperidyl-4-oxycarbonyl)amidino) phenyl]-5-methanesulfonyl-oxymethyl-2-oxazolidinone 3-[4-(N-(1-methylpiperidyl-4-oxycarbonyl)amidino)-phenyl]-5-(4-ethoxycarbonylpiperidinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-ethoxycarbonylpiperidinomethyl)-2-oxazolidinone;

with 3-[4-(N-ethoxycarbonylmethylcarbamoyl-amidino) phenyl]-5-methanesulfonyloxymethyl-2-oxazolidinone 3-[4-(N-ethoxycarbonylmethylcarbamoylamidino) phenyl]-5-(4-ethoxycarbonylpiperidinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(4-ethoxycarbonylpiperidinomethyl)-2-oxazolidinone;

with 3-[4-(N-1-naphthoylamidino)phenyl]-5-methanesulfonyloxymethyl-2-oxazolidinone 3-[4-(N-1-naphthoylamidino)phenyl]-5-(4-ethoxycarbonylpiperidinomethyl)-2-oxazolidinone;

with 3-[4-(N-2-naphthoylamidino)phenyl]-5-methanesulfoniyloxymethyl-2-oxazolidinone 3-[4-(N-2-naphthoylamidino)phenyl-5-(4-ethoxycarbonylpiperidinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(4-ethoxycarbonylpiperidinomethyl)-2-oxazolidinone; m.p. 158–159°, $[\alpha]^D_{20}$=+32.7° (DMSO);

with 3-[4-(N-3-furoylamidino)phenyl]-5-methanesulfonyloxymethyl-2-oxazolidinone 3-[4-(N-3-furoylamidino)phenyl]-5-(4-ethoxycarbonylpiperidinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(4-ethoxycarbonylpiperidinomethyl)-2-oxazolidinone;

with 3-[4-(N-3-thienoylamidino)phenyl]-5-methanesulfonyloxynethyl-2-oxazolidinone 3-[4-(N-3-thienoylamidino)phenyl]-5-(4-ethoxycarbonylpiperidinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(4-ethoxycarbonylpiperidinomethyl)-2-oxazolidinone;

Example 15

In analogy to Example 1, the following are obtained starting from 4-ethoxycarbonylmethyl-4-hydroxypiperidine by reacting with 3-[4-(N-benzyloxycarbonylamidino)phenyl]-5-methanesulfonyloxymethyl-2-oxazolidinone 3-[4-(N-benzyloxycarbonylamidino)phenyl]-5-(4-ethoxycarbonylmethyl-4-hydroxypiperidinomethyl)-2-oxazolidinone;

with 3-(4-(N-benzoylamidino)phenyl]-5-methanesulfonyloxymethyl-2-oxazolidinone 3-[4-(N-benzoylamidino)phenyl]-5-(4-ethoxycarbonylmethyl-4-hydroxypiperidinomethyl)-2-oxazolidinone, m.p. 142°;

with 3-[4-(N-phenoxycarbonylamidino)phenyl]-5-methanesulfonyloxymethyl-2-oxazolidinone 3-[4-(N-phenoxycarbonylamidino)phenyl]-5(4-ethoxycarbonylmethyl-4-hydroxypiperidinomethyl)-2-oxazolidinone;

with 3-[4-(N-(3-pyridylcarbonyl)amidino)phenyl]-5-methanesulfonyloxymethyl-2-oxazolidinone 3-[4-(N-(3-pyridylcarbonyl)amidino)phenyl]-5-(4-ethoxycarbonylmethyl-4-hydroxypiperidinomethyl)-2-oxazolidinone;

with 3-[4-(N-(1-methylpiperidyl-4-oxycarbonyl)amidino)phenyl]-5-methanesulfonyloxymethyl-2-oxazolidinone 3-[4-(N-(1-methylpiperidyl-4-oxycarbonyl)amidino)phenyl]-5-(4-ethoxycarbonylmethyl-4-hydroxypiperidinomethyl)-2-oxazolidinone;

with 3-[4-(N-methoxycarbonylamidino)phenyl]-5-methanesulfonyloxymethyl-2-oxazolidinone 3-[4-(N-methoxycarbonylamidino)phenyl]-5-(4-ethoxycarbonylmethyl-4-hydroxypiperidinomethyl)-2-oxazolidinone;

with 3-[4-(N-ethoxycarbonylmethylcarbamoylamidino)phenyl]-5-methanesulfonyloxymethyl-2-oxazolidinone 3-[4-(N-ethoxycarbonylmethylcarbamoylamidino)phenyl]-5-(4-ethoxycarbonylmethyl-4-hydroxypiperidinomethyl)-2-oxazolidinone;

with 3-[4-(N-methylsulfonylamidino)phenyl]-5-methanesulfonyloxymethyl-2-oxazolidinone 3-[4-(N-methylsulfonylamidino)phenyl]-5-(4-ethoxycarbonylmethyl-4-hydroxypiperidinomethyl)-2-oxazolidinone;

with 3-[4-(N-1-naphthoylamidino)phenyl]-5-methanesulfonyloxymethyl-2-oxazolidinone 3-[4-(N-1-naphthoylamidino)phenyl]-5-(4-ethoxycarbonylmethyl-4-hydroxypiperidinomethyl)-2-oxazolidinone;

with 3-[4-(N-2-naphthoylamidino)phenyl]-5-methanesulfonyloxymethyl-2-oxazolidinone 3-[4-(N-2-naphthoylamidino)phenyl]-5-(4-ethoxycarbonylmethyl-4-hydroxypiperidinomethyl)-2-oxazolidinone;

with 3-[4-(N-2-furoylamidino)phenyl]-5-methanesulfonyloxymethyl-2-oxazolidinone 3-[4-(N-2-furoylamidino)phenyl]-5-(4-ethoxycarbonylmethyl-4-hydroxypiperidinomethyl)-2-oxazolidinone;

with 3-[4-(N-3-furoylamidino)phenyl]-5-methanesulfonyloxymethyl-2-oxazolidinone 3-[4-(N-3-furoylamidino)phenyl]-5-(4-ethoxycarbonylmethyl-4-hydroxypiperidinomethyl)-2-oxazolidinone;

with 3-[4-(N-2-thienoylamidino)phenyl]-5-methanesulfonyloxymethyl-2-oxazolidinone 3-[4-(N-2-thienoylamidino)phenyl]-5-(4-ethoxycarbonylmethyl-4-hydroxypiperidinomethyl)-2-oxazolidinone;

with 3-[4-(N-3-thienoylamidino)phenyl]-5-methanesulfonyloxymethyl-2-oxazolidinone 3-[4-(N-3-thienoylamidino)phenyl]-5-(4-ethoxycarbonylmethyl-4-hydroxypiperidinomethyl)-2-oxazolidinone;

with 3-[4-(N-diphenylacetylamidino)phenyl]-5-methanesulfonyloxymethyl-2-oxazolidinone 3-[4-(N-diphenylacetylamidino)phenyl]-5-(4-ethoxycarbonylmethyl-4-hydroxypiperidinomethyl)-2-oxazolidinone.

Example 16

0.9 g of 3-[4-(5-phenyl-1,2,4-oxadiazolin-3-yl)phenyl]-5-[4-(2-ethoxycarbonyl-2-N-butylsulfonyl-aminoethyl)phenoxymethyl]-2-oxazolidinone [obtainable as in Example 1 by reacting 4-(5-phenyl-1,2,4-oxadiazolin-3-yl)aniline with 2,3-epoxy-1-propanol to give N-[4-(5-phenyl-1,2,4-oxadiazolin-3-yl)phenyl]-2,3-dihydroxypropylamine, reacting with diethyl carbonate in the presence of tert-butoxide to give 3-[4-(5-phenyl-1,2,4-oxadiazolin-3-yl)phenyl]-5-hydroxymethyl-2-oxazolidinone, esterifying with methanesulfonyl chloride and reacting with Na p-(2-ethoxycarbonyl-2-N-butylsulfonylaminoethyl)phenolate] is dissolved in 50 ml of methanol and hydrogenated on Raney nickel. The reaction mixture is subsequently filtered and the filtrate is concentrated in vacuo. The resulting product is treated with 20 ml of hot ethyl acetate and, after cooling, filtered off with suction. 3-[4-(N-benzoylamidino)phenyl]-5-[4-(2-ethoxycarbonyl-2-N-butylsulfonylaminoethyl)phenoxymethyl]-2-oxazolidinone is obtained.

The following are obtained analogously by reductive cleavage of the 5-phenyl-1,2,4-oxadiazoline group starting with 3-[4-(5-phenyl-1,2,4-oxadiazolin-3-yl)phenyl]-5-[4-(2-ethoxycarbonyl-2-N-methylsulfonylaminoethyl)phenoxymethyl]-2-oxazolidinone 3-[4-(N-benzoylamidino)phenyl]-5-[4-(2-ethoxycarbonyl-2-N-methylsulfonylaminoethyl)phenoxymethyl]-2-oxazolidinone;

with 3-[4-(5-phenyl-1,2,4-oxadiazolin-3-yl)phenyl]-5-[4-(2-ethoxycarbonyl-2-α-naphthoylaminoethyl)phenoxymethyl]-2-oxazolidinone 3-[4-(N-benzoylamidino)phenyl]-5-[4-(2-ethoxycarbonyl-2-α-naphthoylaminoethyl)phenoxymethyl]-2-oxazolidinone;

with 3-[4-(5-phenyl-1,2,4-oxadiazolin-3-yl)phenyl]5-[4-(2-ethoxycarbonyl-2-β-naphthoylaminoethyl)-phenoxymethyl]-2-oxazolidinone 3-[4-(N-benzoylamidino)phenyl]-5-[4-(2-ethoxycarbonyl-2-β-naphthoylaminoethyl-phenoxymethyl]-2-oxazolidinone.

Example 17

0.5 g of 1-[4-(5-phenyl-1,2,4-oxadiazolin-3-yl)phenyl]-4-[4-(2-ethoxycarbonylethyl)piperazinol]-piperidine [obtainable by reacting 1-(5-phenyl-1,2,4-oxadiazolin-3-yl)-4-chloropiperidine
with 1-(2-ethoxycarbonylethyl)piperazine] is dissolved in 50 ml of methanol and hydrogenated on Raney nickel. The reaction mixture is then filtered and the filtrate is concentrated in vacuo. The resulting product is treated with 20 ml of hot ethyl acetate and, after cooling, filtered off with suction. 1-[4-(N-benzoylamidino)phenyl-4-[4-(2-ethoxycarbonylethyl)piperazino]piperidine is obtained.

The following are obtained analogously by reductive cleavage of the 5-phenyl-1,2,4-oxadiazoline group starting from 1-[4-(5-phenyl-1,2,4-oxadiazolin-3-yl)phenyl]-4-(1-ethoxycarbonylmethyl-4-piperidinyl)piperazine: 1-[4-(N-benzoylamidino)phenyl]-4-(1-ethoxycarbonylmethyl-4-piperidinyl)piperazine;

from 1-[4-(5-phenyl-1,2,4-oxadiazolin-3-yl)phenyl]-4-[4-(ethoxycarbonylmethyl)piperazinol]piperidine: 1-[4-(N-benzoylamidino)phenyl]-4-[4-(ethoxycarbonylmethyl)piperazino)piperidine;

from 1-[4-(5-phenyl-1,2,4-oxadiazolin-3-yl)phenyl]-4-[1-(2-ethoxycarbonylethyl)-4-piperidinyl]piperazine; 1-[4-(N-benzoylamidino)phenyl]-4-[1-(2-ethoxycarbonylethyl)-4-piperidinyl]piperazine.

Example 18

In analogy to Example 17, 2-oxo-3(S)-ethoxycarbonylmethyl-5(S)-(4-N-benzoylamidino-4'-biphenylyloxymethyl)pyrrolidine is obtained starting from 1.1 g of 2-oxo-3(S)-ethoxycarbonylmethyl-5(S)-[4-(5-phenyl-1,2,4-oxadiazolin-3-yl)-4'-biphenylyloxymethyl]pyrrolidine [obtainable by reacting 4-(5-phenyl-1,2,4-oxadiazolin-3-yl)-4'-hydroxybiphenyl Na salt with 2-oxo-3(S)-ethoxycarbonylmethyl-5(S)-methylsulfonyloxymethylpyrrolidine] by hydrogenation in 50 ml of methanol on Raney nickel and after the usual working up.

The following are obtained analogously by reductive cleavage of the 5-phenyl-1,2,4-oxadiazoline group starting from 2-oxo-3(R)-ethoxycarbonylmethyl-5(S)-[4-(5-phenyl-1,2,4-oxadiazolin-3-yl)-4'-biphenylyloxymethyl]pyrrolidine 2-oxo-3(R)-ethoxycarbonylmethyl-5(S)-(4-N-benzoylamidino-4'-biphenylyloxymethyl)pyrrolidine;

from 2-oxo-3(R)-ethoxycarbonylmethyl-5(R)-[4-(5-phenyl1,2,4-oxadiazolin-3-yl)-4'-biphenylyloxymethyl] pyrrolidine 2-oxo-3(R)-ethoxycarbonylmethyl-5(R)-(4-N-benzoylamidino-4'-biphenylyloxymethyl)pyrrolidine;

from 2-oxo-3(S)-ethoxycarbonylmethyl-5(R)-[4-(5-phenyl-1,2,4-oxadiazolin-3-yl)-4,'-biphenylyloxymethyl)-pyrrolidine 2-oxo-3(S)-ethoxycarbonylmethyl-5(R)-(4-N-benzoylamidino-4'-biphenylyloxymethyl]pyrrolidine.

Example 19

0.7 g of N-[4-(N-benzoylamidino)phenyl]succinamic acid [obtainable by reacting succinic acid monochloride with p-(N-benzoylamidino)aniline] is dissolved in 70 ml of butanol and, in the presence of dicyclohexylcarbodiimide, one equivalent of ethyl 3-amino-4-pentynoate is added. Then, after stirring at room temperature for three hours, the reaction mixture is filtered and the filtrate is concentrated in vacuo. The resulting residue is subjected to the usual working up. N-[4-(N-benzoylamidino)phenyl]-N'-(1-ethoxycarbonyl-methyl-2-propynyl)succinamide is obtained.

The following are obtained analogously by reacting N-[4-(N-benzoylamidino)phenyl]succinamic acid
with 3(S)-amino-4-pentynoate N-[4-(N-benzoylamidino) phenyl]-N-'[1(S)-ethoxycarbonylmethyl-2-propynyl] succinamide;
with 3(R)-amino-4-pentynoate N-[4-(N-benzoylamidino) phenyl]-N'-[1(R)-ethoxycarbonylmethyl-2-propynyl] succinamide;

Example 20

In analogy to Example 16, reductive cleavage of the 5-phenyl-1,2,4-oxadiazoline group in 1,2,4,5-tetrahydro-2-ethoxycarbonylmethyl-3-oxo-4-N-(2-phenylethyl)-8- t4-(5-phenyl-1,2,4-oxadiazolin-3-yl)phenyl-N-methylcarbamoyl] benzodiazepine [obtainable by reacting 1,2,4,5-tetrahydro-2-ethoxycarbonylmethyl-3-oxo-4-N-(2-phenylethyl)-8-carboxybenzodiazepine with 4-(5-phenyl-1,2,4-oxadiazolin-3-yl)-N-methylaniline]and the usual working up resulted in 1,2,4,5-tetrahydro-2-ethoxycarbonylmethyl-3-oxo-4-N-(2-phenylethyl)-8-[4-(N-benzoylamidino)phenyl-N-methylcarbamoyl]benzodiazepine.

Example 21

0.6 g of ethyl 3-[4-(4-(N-benzoylpiperidin-4-yl)butoxy) phenyl]-3-aminopropionate [obtainable by reacting the Na salt of ethyl 3-(4-hydroxyphenyl)-3-N-BOC-amino propionate with 1-chloro-4-(N-benzoyl-4-piperidinyl)butane and subsequently eliminating the protective group] is dissolved in 50 ml of THF, one equivalent of n-butylsulfonyl chloride is added, and the mixture is stirred at room temperature for two hours. The reaction mixture is then subjected to the usual working up to result in ethyl 3-[4-(4-(N-benzoyl-4-piperidin-4-yl)butoxy)phenyl]-3-N-butylsulfonylamino propionate.

Example 22

In analogy to Example 16, 3-[4-(N-benzoylamidino) phenyl]-5-[4-(1,2-di(ethoxycarbonyl)ethyl) piperazinomethyl]-2-oxadiazolinone, m.p. 136°, is obtained starting from 1.1 g of 3-[4-(5-phenyl-1,2,4-oxadiazolin-3-yl)phenyl]-5-[4-(1,2-diethoxycarbonylethyl) piperazinomethyl]-2-oxazolidinone [obtainable by reacting 4-(5-oxo-1,2,4-oxadiazolin-3-yl)aniline with 2,3-epoxy-1-propanol to give N-[4-(S-phenyl-1,2,4-oxadiazolin-3-yl) phenyl]-2,3-dihydroxypropylamine, reacting with diethyl carbonate in the presence of tert-butoxide to give 3-[4-(5-phenyl-1,2,4-oxadiazolin-3-yl)phenyl]-5-hydroxymethyl-2-oxazolidinone, esterifying with methanesulfonyl chloride and reacting with 1-(1,2-diethoxycarbonylethyl)piperazine] by hydrogenation on Raney nickel and the usual working up.

The following are obtained analogously by reductive cleavage of the 5-phenyl-1,2,4-oxadiazoline group
from 3-[4-(5-phenyl-1,2,4-oxadiazolin-3-yl)phenyl]-5-[4-(1-carboxy-2-ethoxycarbonylethyl)piperazinomethyl]-2-oxazolidinone 3-[4-(N-benzoylamidino)phenyl]-5-[4-(1-carboxy-2-ethoxycarbonylethyl)piperazinomethyl]-2-oxazolidinone;
from 3-[4-(5-phenyl-1,2,4-oxadiazolin-3-yl)phenyl]-5-[4-(2-carboxy-1-ethoxycarbonylethyl)piperazinomethyl]-2-oxazolidinone 3-[4-(N-benzoylamidino)phenyl]-5-[4-(2-carboxy-1-ethoxycarbonylethyl)piperazinomethy]-2-oxazolidinone;
from 3-[4-(5-methyl-1,2,4-oxadiazolin-3-yl)phenyl]-5-(4-(1,2-diethoxycarbonylethyl)piperazinomethyl]-2-oxazolidinone 3-[4-(N-acetylamidino)phenyl]-5-[4-(1,2-diethoxycarbonylethyl)piperazinomethyl]-2-oxazolidinone;
from 3-[4-(5-methyl-1,2,4-oxadiazolin-3-yl)phenyl]-5-(4-(1-carboxy-2-ethoxycarbonylethyl)piperazinomethyl]-2-oxazolidinone
from 3-[4-(N-acetylamidino)phenyl]-5-[4-(1-carboxy-2-ethoxycarbonylethyl)piperazinomethyl]-2-oxazolidinone;
from 3-[4-(5-methyl-1,2,4-oxadiazolin-3-yl)phenyl]-5-(4-(2-carboxy-1-ethoxycarbonylethyl)piperazinomethyl]-2-oxazolidinone 3-[4-(N-acetylamidino)phenyl]-5-[4-(2-carboxy-1-ethoxycarbonylethyl)piperazinomethyl]-2-oxazolidinone;
from 3-[4-(5-ethyl-1,2,4-oxadiazolin-3-yl)phenyl]-5-[4-(1,2-diethoxycarbonylethyl)piperazinomethyl]-2-oxazolidinone 3-[4-(N-propionylamidino)phenyl)-5-[4-(1,2-diethoxycarbonylethyl)piperazinomethyl]-2-oxazolidinone;
from 3-[4-(5-ethyl-1,2,4-oxadiazolin-3-yl)phenyl]-5-[4-(1-carboxy-2-ethoxycarbonylethyl)piperazinomethyl]-2-oxazolidinone 3-[4-(N-propionylamidino)phenyl]-5-[4-(1-carboxy-2-ethoxycarbonylethyl)piperazinomethyl]-2-oxazolidinone;
from 3-[4-(5-ethyl-1,2,4-oxadiazolin-3-yl)phenyl]-5-[4-(2-carboxy-1-ethoxycarbonylethyl)piperazinomethyl]-2-oxazolidinone 3-[4-(N-propionylamidino)phenyl]-5-[4-(2-carboxy-1-ethoxycarbonylethyl)piperazinomethyl]-2-oxazolidinone;
from 3-[4-(5-(3-pyridyl)-1,2,4-oxadiazolin-3-yl)phenyl]-5-[4-(1,2-diethoxycarbonylethyl)piperazinomethyl]-2-oxazolidinone 3-[4-(N-(3-pyridyl)amidino)phenyl)-5-[4-(1,2-diethoxycarbonylethyl)piperazinomethyl]-2-oxazolidinone;
from 3-[4-(5-(3-pyridyl)-1,2,4-oxadiazolin-3-yl)phenyl]-5-[4-(1-carboxy-2-ethoxycarbonylethyl)piperazinomethyl]-2-oxazolidinone 3-[4-(N-(3-pyridyl)amidino)phenyl]-5-[4-(1-carboxy-2-ethoxycarbonylethyl)piperazinomethyl]-2-oxazolidinone;
from 3-[4-(5-(3-pyridyl)-1,2,4-oxadiazolin-3-yl)phenyl]-5-[4-(2-carboxy-1-ethoxycarbonylethyl)piperazinomethyl]-2-oxazolidinone 3-[4-(N-(3-pyridyl)amidino)phenyl]-5-[4-(2-carboxy-1-ethoxycarbonylethyl)piperazinomethyl]-2-oxazolidinone.

Example 23

In analogy to Example 16, 1-[3-(4-hydroxyphenyl)-2-N-(4-(N-benzoylamidino)benzoyl)aminopropionyl)-4-

(ethoxycarbonylmethoxy)piperidine is obtained starting from 0.8 g of 1-[3-(4-hydroxyphenyl)-2-N-(4-(5-phenyl-1, 2,4-oxadiazolin-3-yl)benzoyl)aminopropionyl]-4-(ethoxycarbonylmethoxy)piperidine [obtainable by reacting 3-(4-hydroxyphenyl)-2-N-(4-(5-phenyl-1,2,4-oxadiazolin-3-yl)benzoyl)aminopropionyl chloride with 4-(ethoxycarbonylmethoxy)piperidine] by hydrogenation on Raney nickel and the usual working up.

The following are obtained analogously by reductive cleavage of the 5-phenyl-1,2,4-oxadiazoline group
from 1-[3-phenyl-2-N-(4-(5-phenyl-1,2,4-oxadiazolin-3-yl) benzoyl)aminopropionyl]-4-(ethoxycarbonylmethoxy) piperidine 1-[3-phenyl-2-N-(4-(N-benzoylamindino) benzoyl)aminopropionyl]-4-ethoxycarbonylmethoxy) piperidine;
from 1-[2-N-(4-(5-phenyl-1,2,4-oxadiazolin-3-yl)benzoyl) aminopropionyl]-4-(ethoxycarbonylmethoxy)piperidine 1-[2-N-(4-(N-benzoylamidino)benzoyl)aminopropionyl]-4-(ethoxycarbonylmethoxy)piperidine;
from 1-[2-N-(4-(5-phenyl-1,2,4-oxadiazolin-3-yl)benzoyl) aminoacetyl]-4-(ethoxycarbonylmethoxy)piperidine 1-[2-N-(4-(N-benzoylamidino)benzoyl)aminoacetyl]-4-(ethoxycarbonylmethoxy)piperidine.

Example 24

0.8 g of 3-[4-(N-benzoylamidino)phenyl]-5-[4-(1,2-diethoxycarbonylethyl)piperazinomethyl]-2-oxazolidinone [obtainable as described in Example 22] is suspended in 60 ml of methanol, 10 ml of 2 N NaOH solution are added and the mixture is stirred at room temperature for 4 hours. After removal of the solvent, the residue is taken up in water, the pH is adjusted to 3 by adding dilute HCl, and the reaction mixture is filtered through an ion exchanger. The filtrate is dried over $MgSO_4$. Removal of the solvent and subsequent freeze-drying result in 3-[4-(N-benzoylamidino)phenyl]-5-[4-(1,2-dicarboxyethyl)piperazinomethyl]-2-oxazolidinone.

The following are obtained analogously by hydrolysis:
from 3-[4-(N-acetylamidino)phenyl]-5-[4-(1,2-diethoxycarbonylethyl)piperazinomethyl]-2-oxazolidinone 3-[4-(N-acetylamidino)phenyl]-5-[4-(1,2-dicarboxyethyl)piperazinomethyl]-2-oxazolidinone;
from 3-[4-(N-propionylamidino)phenyl -5-[4-(1,2-diethoxycarbonylethyl)piperazinomethyl]-2-oxazolidinone 3-[4-(N-propionylamidino)phenyl]-5-[4-(1,2-dicarboxyethyl)piperazinomethyl]-2-oxazolidinone;
from 3-[4-(N-(3-pyridyl)amidino)phenyl]-5-[4-(1,2-diethoxycarbonylethyl)piperazinomethyl]-2-oxazolidinone 3-[4-(N-(3-pyridyl)amidino)phenyl]-5-[4-(1,2-5 dicarboxyethyl)piperazinomethyl]-2-oxazolidinone.

Example 25

In analogy to Example 1, the following are obtained by reacting 4-ethoxycarbonylmethylpiperazine ("A")
with 3-[4-(N-4-chlorobenzoylamidino)phenyl]-5-methanesulfonyloxymethyl-2-oxazolidinone 3-[4-(N-4-chlorobenzoylamidino)phenyl]-5-(4-ethoxycarbonylmethylpiperazinomethyl)-2-oxazolidinone;
with 3-[4-(N-4-fluorobenzoylamidino)phenyl]-5-methanesulfonyloxymethyl-2-oxazolidinone 3-[4-(N-4-fluorobenzoylamidino)phenyl]-5-(4-ethoxycarbonylmethylpiperazinomethyl)-2-oxazolidinone;
with 3-[4-(N-4-methoxybenzoylamidino)phenyl]-5-methanesulfonyloxymethyl-2-oxazolidinone 3-[4-(N-4-methoxybenzoylamidino)phenyl]-5-(4-ethoxycarbonylmethylpiperazinomethyl)-2-oxazolidinone, m.p. 115–120°;
with 3-[4-(N-3,4-methylenedioxybenzoylamidino)phenyl]-5-methanesulfonyloxymethyl-2-oxazolidinone 3-[4-(N-3,4-methylenedioxybenzoylamidino)phenyl]-5-(4-ethoxycarbonylmethylpiperazinomethyl)-2-oxazolidinone, m.p. 168–169°;
with 3-[4-(N-4-trifluoromethylbenzoylamidino)phenyl]-5-methanesulfonyloxymethyl-2-oxazolidinone 3-(4-(N-4-trifluoromethylbenzoylamidino)phenyl]-5-(4-ethoxycarbonylmethylpiperazinomethyl)-2-oxazolidinone;
with 3-[4-(N-4-cyanobenzoylamidino)phenyl]-5-methanesulfonyloxymethyl-2-oxazolidinone 3-[4-(N-4-cyanobenzoylamidino)phenyl]-5-(4-ethoxycarbonylmethylpiperazinomethyl)-2-oxazolidinone;
with 3-[4-(N-4-methoxybenzoylamidino)phenyl]-5(R)-methanesulfonyloxymethyl-2-oxazolidinone 3-[4-(N-4-methoxybenzoylamidino)phenyl]-5(R)-(4-ethoxycarbonylmethylpiperazinomethyl)-2-oxazolidinone, m.p. 153–154°, $[\alpha]^D_{20}$=+31,2° (DMSO);
with 3-[4-(N-4-nitrobenzoylamidino)phenyl]-5-methanesulfonyloxymethyl-2-oxazolidinone 3-[4-(N-4-nitrobenzoylamidino)phenyl]-5-(4-ethoxycarbonylmethylpiperazinomethyl)-2-oxazolidinone;
with 3-[4-(N-4-methylbenzoylamidino)phenyl]-5methanesulfonyloxymethyl-2-oxazolidinone 3-[4-(N-4-methylbenzoylamidino)phenyl]-5-(4-ethoxycarbonylmethylpiperazinomethyl)-2-oxazolidinone;
with 3-[4-(N-4-methoxycarbonylbenzoylamidino)phenyl]-5-methanesulfonyloxymethyl-2-oxazolidinone 3-[4-(N-4-methoxycarbonylbenzoylamidino)phenyl]-5-(4-ethoxycarbonylmethylpiperazinomethyl)-2-oxazolidinone;
with 3-[4-(N-4-tert-butylbenzoylamidino)phenyl]-5-methanesulfonyloxymethyl-2-oxazolidinone 3-[4-(N-4-tert-butylbenzoylamidino)phenyl]-5-(4-ethoxycarbonylmethylpiperazinomethyl)-2-oxazolidinone;
with 3-[4-(N-3-chlorobenzoylamidino)phenyl]-5-methanesulfonyloxymethyl-2-oxazolidinone 3-[4-(N-3-chlorobenzoylamidino)phenyl]-5-(4-ethoxycarbonylmethylpiperazinomethyl)-2-oxazolidinone;
with 3-[4-(N-3-fluorobenzoylamidino)phenyl]-5-methanesulfonyloxymethyl-2-oxazolidinone 3-[4-(N-3-fluorobenzoylamidino)phenyl]-5-(4-ethoxycarboriylmethylpiperazinomethyl)-2-oxazolidinone;
with 3-[4-(N-3-methoxybenzoylamidino)phenyl]-5-methanesulfonyloxymethyl-2-oxazolidinone 3-[4-(N-3-methoxybenzoylamidino)phenyl]-5-(4-ethoxycarbonylmethylpiperazinomethyl)-2-oxazolidinone;
with 3-[4-(N-3,4-dimethoxybenzoylamidino)phenyl]-5-methanesulfonyloxymethyl-2-oxazolidinone 3-[4-(N-3,4-dimethoxybenzoylamidino)phenyl]-5-(4-ethoxycarbonylmethylpiperazinomethyl)-2-oxazolidinone;
with 3-[4-(N-3-trifluoromethylbenzoylamidino)phenyl]-5 (R)-methanesulfonyloxymethyl-2-oxazolidinone 3-[4-(N-3-trifluoromethylbenzoylamidino)phenyl]-5(R)-(4-ethoxycarbonylmethylpiperazinomethyl)-2-oxazolidinone, m.p. 128–129°, $[\alpha]^D_{20}$=+29,7° (DMSO);

with 3-[4-(N-3-cyanobenzoylamidino)phenyl]-5-methanesulfonyloxymethyl-2-oxazolidinone 3-[4-(N-3-cyanobenzoylamidino)phenyl]-5-(4-ethoxycarbonylmethylpiperazinomethyl)-2-oxazolidinone;

with 3-[4-(N-3-nitrobenzoylamidino)phenyl]-5-methanesulfonyloxymethyl-2-oxazolidinone 3-[4-(N-3-nitrobenzoylamidino)phenyl]-5-(4-ethoxycarbonylmethylpiperazinomethyl)-2-oxazolidinone;

with 3-[4-(N-3-methylbenzoylamidino)phenyl]-5-methanesulfonyloxymethyl-2-oxazolidinone 3-[4-(N-3-methylbenzoylamidino)phenyl]-5-(4-ethoxycarbonylmethylpiperazinomethyl)-2-oxazolidinone;

with 3-[4-(N-3-methoxycarbonylbenzoylamidino)phenyl]-5-methanesulfonyloxymethyl-2-oxazolidinone 3-[4-(N-3-methoxycarbonylbenzoylamidino)phenyl]-5-(4-ethoxycarbonylmethylpiperazinomethyl)-2-oxazolidinone;

with 3-[4-(N-3-tert-butylbenzoylamidino)phenyl]-5-methanesulfonyloxymethyl-2-oxazolidinone 3-[4-(N-3-tert-butylbenzoylamidino)phenyl]-5-(4-ethoxycarbonylmethylpiperazinomethyl)-2-oxazolidinone;

with 3-[4-(N-2-chlorobenzoylamidino)phenyl]-5-methanesulfonyloxymethyl-2-oxazolidinone 3-[4-(N-2-chlorobenzoylamidino)phenyl]-5-(4-ethoxycarbonylmethylpiperazinomethyl)-2-oxazolidinone;

with 3-[4-(N-2-fluorobenzoylamidino)phenyl]-5-methanesulfonyloxymethyl-2-oxazolidinone 3-[4-(N-2-fluorobenzoylamidino)phenyl]-5-(4-ethoxycarbonylmethylpiperazinomethyl)-2-oxazolidinone;

with 3-[4-(N-2-methoxybenzoylamidino)phenyl]-5-methanesulfonyloxymethyl-2-oxazolidinone 3-[4-(N-2-methoxybenzoylamidino)phenyl]-5-(4-ethoxycarbonylmethylpiperazinomethyl)-2-oxazolidinone;

with 3-[4-(N-2,3,4-trimethoxybenzoylamidino)phenyl]-5-methanesulfonyloxymethyl-2-oxazolidinone 3-[4-(N-2,3,4-trimethoxybenzoylamidino)phenyl]-5-[4-ethoxycarbonylmethylpiperazinomethyl)-2-oxazolidinone;

with 3-[4-(N-2-trifluoromethylbenzoylamidino)phenyl]-5-methanesulfonyloxymethyl-2-oxazolidinone 3-[4-(N-2-trifluoromethylbenzoylamidino)phenyl]-5-[4-ethoxycarbonylmethylpiperazinomethyl)-2-oxazolidinone, m.p 121°;

with 3-[4-(N-2-cyanobenzoylamidino)phenyl]-5-methanesulfonyloxymethyl-2-oxazolidinone 3-[4-(N-2-cyanobenzoylamidino)phenyl]-5-(4-ethoxycarbonylmethylpiperazinomethyl)-2-oxazolidinone;

with 3-[4-(N-2-nitrobenzoylamidino)phenyl]-5-methanesulfonyloxymethyl-2-oxazolidinone 3-[4-(N-2-nitrobenzoylamidino)phenyl]-5-(4-ethoxycarbonylmethylpiperazinomethyl)-2-oxazolidinone;

with 3-[4-(N-2-methylbenzoylamidino)phenyl]-5-methanesulfonyloxymethyl-2-oxazolidinone 3-[4-(N-2-methylbenzoylamidino)phenyl]-5-(4-ethoxycarbonylmethylpiperazinomethyl)-2-oxazolidinone;

with 3-[4-(N-2-methoxycarbonylbenzoylamidino)phenyl]-5-methanesulfonyloxymethyl-2-oxazolidinone 3-[4-(N-2-methoxycarbonylbenzoylamidino)phenyl]-5-(4-ethoxycarbonylmethylpiperazinomethyl)-2-oxazolidinone;

with 3-[4-(N-2-tert-butylbenzoylamidino)phenyl]-5-methanesulfonyloxymethyl-2-oxazolidinone 3-[4-(N-2-tert-butylbenzoylamidino)phenyl]-5-(4-ethoxycarbonylmethylpiperazinomethyl)-2-oxazolidinone.

Example 26

In analogy to Example 24, the following acid derivatives are obtained by hydrolysis with the 4-ethoxycarbonylethylpiperazines from Example 2:

3-[4-(N-benzoylamidino)phenyl]-5-(4-carboxyethylpiperazinomethyl)-2-oxazolidinone, ditrifluoroacetate, m.p. 172°;

3-[4-(N-benzyloxycarbonylamidino)phenyl]-5-(4-carboxyethylpiperazinomethyl)-2-oxazolidinone, ditrifluoroacetate, m.p. 134°;

3-[4-(N-phenoxycarbonylamidino)phenyl]-5-(4-carboxyethylpiperazinomethyl)-2-oxazolidinone;

3-[4-(N-(3-pyridylcarbonyl)amidino)phenyl]-5-(4-carboxyethylpiperazinomethyl)-2-oxazolidinone;

3-[4-(N-(1-methyl-4-piperidyloxycarbonyl)amidino)phenyl]-5-(4-carboxyethylpiperazinomethyl)-2-oxazolidinone;

3-[4-(N-methoxycarbonylamidino)phenyl]-5-(4-carboxyethylpiperazinomethyl)-2-oxazolidinone, ditrifluoroacetate dihydrate, m.p. 99–100°;

3-[4-(N-ethoxycarbonylmethylcarbamoylamidino)phenyl]-5-(4-carboxyethylpiperazinomethyl)-2-oxazolidinone, m.p. 102°;

3-[4-(N-methylsulfonylamidino)phenyl]-5-(4-carboxyethylpiperazinomethyl)-2-oxazolidinone, ditrifluoroacetate hydrate, m.p. 174°;

3-[4-(N-1-naphthoylamidino)phenyl]-5-(4-carboxyethylpiperazinomethyl)-2-oxazolidinone, ditrifluoroacetate, m.p. 111–113°;

3-[4-(N-2-naphthoylamidino)phenyl]-5-(4-carboxyethylpiperazinomethyl)-2-oxazolidinone;

3-[4-(N-diphenylacetylamidino)phenyl]-5-(4-carboxyethylpiperazinomethyl)-2-oxazolidinone, ditrifluoroacetate, m.p. 80–83°.

Example 27

In analogy to Example 1, the following is obtained by reacting 4-ethoxycarbonylmethylpiperazine ("A") with 3-[4-(N-2-acetoxybenzoylamidino)phenyl]-5-methanesulfonyloxymethyl-2-oxazolidinone 3-[4-(N-2-acetoxybenzoylamidino)phenyl]-5-(4-ethoxycarbonylmethylpiperazinomethyl)-2-oxazolidinone.

Example 28

In analogy to Example 1, the following is obtained by reacting 4-ethoxycarbonylethylpiperazine with 3-[4-(N-2-acetoxybenzoylamidino)phenyl]-5-methanesulfonyloxymethyl-2-oxazolidinone 3-[4-(N-2-acetoxybenzoylamidino)phenyl]-5-(4ethoxycarbonylethylpiperazinomethyl)-2-oxazolidinone.

Example 29

In analogy to Example 1, the following is obtained by reacting 4-(2-acetoxyphenoxycarbonyl)piperidine with 3-[4-(N-2-acetoxybenzoylamidino)phenyl]-5-methanesulfonyloxymethyl-2-oxazolidinone 3-[4-(N-2-acetoxybenzoylamidino)phenyl]-5-[4-(2-acetoxyphenoxycarbonyl)piperidino]-2-oxazolidinone.

Example 30

In analogy to Example 11 the following is obtained by reacting 4-(2-acetoxyphenoxycarbonyl) piperidine with 3-[4-(N-benzoylamidino)phenyl]-5-methanesulfonyloxymethyl-2-oxazolidinone 3-[4-(N-benzoylamidino)phenyl]-5-[4-(2-acetoxyphenoxycarbonyl)piperidino]-2-oxazolidinone.

Example 31

In analogy to Example 1, the following is obtained by reacting 4-(2-acetoxyphenoxycarbonylmethyl)piperazine with 3-[4-(N-2-acetoxybenzoylamidino)phenyl]-5-methanesulfonyloxymethyl-2-oxazolidinone 3-[4-(N-2-acetoxybenzoylamidino)phenyl]-5-[4-(2-acetoxyphenoxycarbonylmethyl)piperazinomethyl)-2-oxazolidinone.

Example 32

In analogy to Example 1, the following is obtained by reacting 4-(2-acetoxyphenoxycarbonylethyl)piperazine with 3-[4-(N-2-acetoxybenzoylamidino)phenyl]-5-methanesulfonyloxymethyl-2-oxazolidinone 3-[4-(N-2-acetoxybenzoylamidino)phenyl]-5-[4-(2-acetoxyphenoxycarbonylethyl)piperazinomethyl)-2-oxazolidinone.

Example 33

In analogy to Example 1, the following is obtained by reacting 4-(2-acetoxyphenoxycarbonylmethyl)piperazine with 3-[4-(N-benzoylamidino)phenyl]-5-methanesulfonyloxymethyl-2-oxazolidinone 3-[4-(N-benzoylamidino)phenyl]-5-[4-(2-acetoxyphenoxycarbonylmethyl)piperazinomethyl)-2-oxazolidinone.

Example 34

In analogy to Example 1, the following is obtained by reacting 4-(2-acetoxyphenoxycarbonylethyl)piperazine with 3-[4-(N-benzoylamidino)phenyl]-5-methanesulfonyloxymethyl-2-oxazolidinone 3-[4-(N-benzoylamidino)phenyl]-5-[4-(2-acetoxyphenoxycarbonylethyl)piperazinomethyl)-2-oxazolidinone.

Example 35

In analogy to Example 1, the following are obtained by reacting 4-ethoxycarbonylethylpiperazine with 3-[4-(N-4-chlorobenzoylamidino)phenyl]-5-methanesulfonyloxymethyl-2-oxazolidinone 3-[4-(N-4-chlorobenzoylamidino)phenyl]-5-(4-ethoxycarbonylethylpiperazinomethyl)-2-oxazolidinone;
with 3-[4-(N-4-fluorobenzoylamidino)phenyl]-5-methanesulfonyloxymethyl-2-oxazolidinone 3-[4-(N-4-fluorobenzoylamidino)phenyl]-5-(4-ethoxycarbonylethylpiperazinomethyl)-2-oxazolidinone;
with 3-[4-(N-4-methoxybenzoylamidino)phenyl]-5-methanesulfonyloxymethyl-2-oxazolidinone 3-[4-(N-4-methoxybenzoylamidino)phenyl]-5-(4-ethoxycarbonylethylpiperazinomethyl)-2-oxazolidinone, m.p. 147–150°;
with 3-[4-(N-3,4-methylenedioxybenzoylamidino)phenyl]-5-methanesulfonyloxymethyl-2-oxazolidinone 3-[4-(N-3,4-methylenedioxybenzoylamidino)phenyl]-5-(4-ethoxycarbonylethylpiperazinomethyl)-2-oxazolidinone;
with 3-[4-(N-4-trifluoromethylbenzoylamidino)phenyl]-5-methanesulfonyloxymethyl-2-oxazolidinone 3-[4-(N-4-trifluoromethylbenzoylamidino)phenyl]-5-(4-ethoxycarbonylethylpiperazinomethyl)-2-oxazolidinone, m.p. 187°;
with 3-[4-(N-4-cyanobenzoylamidino)phenyl]-5-methanesulfonyloxymethyl-2-oxazolidinone 3-[4-(N-4-cyanobenzoylamidino)phenyl]-5-(4-ethoxycarbonylethylpiperazinomethyl)-2-oxazolidinone;
with 3-[4-(N-4-nitrobenzoylamidino)phenyl]-5-methanesulfonyloxymethyl-2-oxazolidinone 3-[4-(N-4-nitrobenzoylamidino)phenyl]-5-(4-ethoxycarbonylethylpiperazinomethyl)-2-oxazolidinone;
with 3-[4-(N-4-methylbenzoylamidino)phenyl]-5-methanesulfonyloxymethyl-2-oxazolidinone 3-[4-(N-4-methylbenzoylamidino)phenyl]-5-(4-ethoxycarbonylethylpiperazinomethyl)-2-oxazolidinone;
with 3-[4-(N-4-methoxycarbonylbenzoylamidino)phenyl]-5-methanesulfonyloxymethyl-2-oxazolidinone 3-[4-(N-4-methoxycarbonylbenzoylamidino)phenyl-5-(4-ethoxycarbonylethylpiperazinomethyl)-2-oxazolidinone;
with 3-[4-(N-4-tert-butylbenzoylamidino)phenyl]-5-methanesulfonyloxymethyl-2-oxazolidinone 3-[4-(N-4-tert-butylbenzoylamidino)phenyl]-5-(4-ethoxycarbonylethylpiperazinomethyl)-2-oxazolidinone;
with 3-[4-(N-3-chlorobenzoylamidino)phenyl]-5-methanesulfonyloxymethyl-2-oxazolidinone 3-[4-(N-3-chlorobenzoylamidino)phenyl]-5-(4ethoxycarbonylethylpiperazinomethyl)-2-oxazolidinone;
with 3-[4-(N-3-fluorobenzoylamidino)phenyl]-5-methanesulfonyloxymethyl-2-oxazolidinone 3-[4-(N-3-fluorobenzoylamidino)phenyl]-5-(4-ethoxycarbonylethylpiperazinomethyl)-2-oxazolidinone;
with 3-[4-(N-3-methoxybenzoylamidino)phenyl]-5-methanesulfonyloxymethyl-2-oxazolidinone 3-[4-(N-3-methoxybenzoylamidino)phenyl]-5-(4-ethoxycarbonylethylpiperazinomethyl)-2-oxazolidinone;
with 3-[4-(N-3,4-dimethoxybenzoylamidino)phenyl]-5-methanesulfonyloxymethyl-2-oxazolidinone 3-[4-(N-3,4-dimethoxybenzoylamidino)phenyl]-5(4-ethoxycarbonylethylpiperazinomethyl)-2-oxazolidinone;
with 3-[4-(N-3-trifluoromethylbenzoylamidino)phenyl]-5-methanesulfonyloxymethyl-2-oxazolidinone 3-[4-(N-3-trifluoromethylbenzoylamidino)phenyl]-5-(4-ethoxycarbonylethylpiperazinomethyl)-2-oxazolidinone, 130–131°;
with 3-[4-(N-3-cyanobenzoylamidino)phenyl]-5-methanesulfonyloxymethyl-2-oxazolidinone 3-[4-(N-3-cyanobenzoylamidino)phenyl]-5-(4-ethoxycarbonylethylpiperazinomethyl)-2-oxazolidinone;
with 3-[4-(N-3-nitrobenzoylamidino)phenyl]-5-methanesulfonyloxymethyl-2-oxazolidinone 3-[4-(N-3-nitrobenzoylamidino)phenyl)-5-(4-ethoxycarbonylethylpiperazinomethyl)-2-oxazolidinone;
with 3-[4-(N-3-methylbenzoylamidino)phenyl]-5-methanesulfonyloxymethyl-2-oxazolidinone 3-[4-(N-3-methylbenzoylamidino)phenyl]-5(4-ethoxycarbonylethylpiperazinomethyl)-2-oxazolidinone;
with 3-[4-(N-3-methoxycarbonylbenzoylamidino)phenyl]-5-methanesulfonyloxymethyl-2-oxazolidinone 3-[4-(N-

3-methoxycarbonylbenzoylamidino)phenyl]-5-(4-ethoxycarbonylethylpiperazinomethyl)-2-oxazolidinone;
with 3-[4-(N-3-tert-butylbenzoylamidino)phenyl]-5-methanesulfonyloxymethyl-2-oxazolidinone 3-[4-(N-3-tert-butylbenzoylamidino)phenyl]-5-(4-ethoxycarbonylethylpiperazinomethyl)-2-oxazolidinone;
with 3-[4-(N-2-chlorobenzoylamidino)phenyl]-5-methanesulfonyloxymethyl-2-oxazolidinone 3-[4-(N-2-chlorobenzoylamidino)phenyl]-5-(4-ethoxycarbonylethylpiperazinomethyl)-2-oxazolidinone;
with 3-[4-(N-2-fluorobenzoylamidino)phenyl]-5-methanesulfonyloxymethyl-2-oxazolidinone 3-[4-(N-2-fluorobenzoylamidino)phenyl]-5-(4-ethoxycarbonylethylpiperazinomethyl)-2-oxazolidinone;
with 3-[4-(N-2-methoxybenzoylamidino)phenyl]-5-methanesulfonyloxymethyl-2-oxazolidinone 3-[4-(N-2-methoxybenzoylamidino)phenyl]-5-(4-ethoxycarbonylethylpiperazinomethyl)-2-oxazolidinone;
with 3-[4-(N-2,3,4-trimethoxybenzoylamidino)phenyl]-5-methanesulfonyloxymethyl-2-oxazolidinone 3-[4-(N-2,3,4-trimethoxybenzoylamidino)phenyl]-5-(4-ethoxycarbonylethylpiperazinomethyl)-2-oxazolidinone;
with 3-[4-(N-2-trifluoromethylbenzoylamidino)phenyl]-5-methanesulfonyloxymethyl-2-oxazolidinone 3-[4-(N-2-trifluoromethylbenzoylamidino)phenyl]-5-(4-ethoxycarbonylethylpiperazinomethyl)-2-oxazolidinone;
with 3-[4-(N-2-cyanobenzoylamidino)phenyl]-5-methanesulfonyloxymethyl-2-oxazolidinone 3-[4-(N-2-cyanobenzoylamidino)phenyl]-5-(4-ethoxycarbonylethylpiperazinomethyl)-2-oxazolidinone;
with 3-[4-(N-2-nitrobenzoylamidino)phenyl]-5-methanesulfonyloxymethyl-2-oxazolidinone 3-[4-(N-2-nitrobenzoylamidino)phenyl]-5-(4-ethoxycarbonylethylpiperazinomethyl)-2-oxazolidinone;
with 3-[4-(N-2-methylbenzoylamidino)phenyl]-5-methanesulfonyloxymethyl-2-oxazolidinone 3-[4-(N-2-methylbenzoylamidino)phenyl]-5-(4-ethoxycarbonylethylpiperazinomethyl)-2-oxazolidinone;
with 3-[4-(N-2-methoxycarbonylbenzoylamidino)phenyl]-5-methanesulfonyloxymethyl-2-oxazolidinone 3-[4-(N-2-methoxycarbonylbenzoylamidino)phenyl]-5-(4-ethoxycarbonylethylpiperazinomethyl)-2-oxazolidinone;
with 3-[4-(N-2-tert-butylbenzoylamidino)phenyl]-5-methanesulfonyloxymethyl-2-oxazolidinone 3-[4-(N-2-tert-butylbenzoylamidino)phenyl]-5-(4-ethoxycarbonylethylpiperazinomethyl)-2-oxazolidinone.

Example 36

In analogy to Example 1, the following is obtained by reacting 4-tert.-butoxycarbonylmethyl-piperazine
with 3-[4-(N-benzoylamidino)phenyl]-5(R)-methanesulfonyloxymethyl-2-oxazolidinone 3-[4-(N-benzoylamidino)phenyl]-5(R)-(4-tert.-butoxycarbonylmethylpiperazino-methyl)-2-oxazolidinone, m.p. 160°, $[\alpha]_{20}$=+32,7°;
with 3-[4-(N-benzoylamidino)phenyl]-5-methanesulfonyloxymethyl-2-oxazolidinone 3-[4-(N-benzoylamidino)phenyl]-5-(4-tert.-butoxycarbonylmethylpiperazinomethyl)-2-oxazolidinone, m.p. 182°.

Example 37

In analogy to Example 1, the following is obtained by reacting 4-methoxycarbonylmethyl-phenolat-sodium salt
with 3-[4-(N-benzoylamidino)phenyl]-5-chloromethyl-2-oxazolidinone 3-[4-(N-benzoylamidino)phenyl)-5-(4-methoxycarbonylmethyl-phenoxymethyl)-2-oxazolidinone, m.p. 170°.

In analogy to Example 1, the following is obtained by reacting 4-(1-methoxycarbonyl-1-N-butylsulfonylaminoethyl)-phenolat-sodium salt
with 3-[4-(N-benzoylamidino)phenyl]-5-chloromethyl-2-oxazolidinone 3-[4-(N-benzoylamidino)phenyl]-5-[4-(1-methoxycarbonyl-1-N-butylsulfonylamino-ethyl-phenoxymethyl)-2-oxazolidinone.

Example 38

In analogy to Example 1, the following is obtained by reacting 1-ethoxycarbonylmethyl-piperazine
with 3-[4-(N-ethoxycarbonylamidino)phenyl]-5(R)-chloromethyl-2-oxazolidinone 3-[4-(N-ethoxycarbonylamidino)phenyl]-5(R)-(4-ethoxycarbonylmethyl-piperazinomethyl)-2-oxazolidinone, m.p. 142–143°;
with 3-[4-(N-ethoxycarbonylamidino)phenyl]-5(S)-chloromethyl-2-oxazolidinone 3-[4-(N-ethoxycarbonylamidino)phenyl]-5(S)-(4-ethoxycarbonylmethyl-piperazinomethyl)-2-oxazolidinone;
with 3-[4-(N-isopropoxycarbonylamidino)phenyl)-5(R)-chloromethyl-2-oxazolidinone 3-[4-(N-isopropoxycarbonylamidino)phenyl-5(R)-(4-ethoxycarbonylmethyl-piperazinomethyl)-2-oxazolidinone, m.p. 129–130°, $[\alpha]^{P}_{20}$32 +31,2° (DMSO);
with 3-[4-(N-isopropoxycarbonylamidino)phenyl]-5(S)-chloromethyl-2-oxazolidinone 3-[4-(N-isopropoxycarbonylamidino)phenyl]-5(S)-(4-ethoxycarbonylmethyl-piperazinomethyl)-2-oxazolidinone;
with 3-[4-(N-methoxycarbonylamidino)phenyl]-5(R)-chloromethyl-2-oxazolidinone 3-[4-(N-methoxycarbonylamidino)phenyl]-5(R)-(4-ethoxycarbonylmethyl-piperazinomethyl)-2-oxazolidinone, m.p. 175–176°, $[\alpha]^{P}_{20}$=+51° (methanol);
with 3-[4-(N-methoxycarbonylamidino)phenyl]-5(S)-chloromethyl-2-oxazolidinone 3-[4-(N-methoxycarbonylamidino)phenyl]-5(S)-(4ethoxycarbonylmethyl-piperazinomethyl)-2-oxazolidinone;
In analogy, the following is obtained by reacting 1-tert.-butoxycarbonylmethylpiperazine
with 3-[4-(N-methoxycarbonylamidino)phenyl)-5-chloromethyl-2-oxazolidinone 3-[4-(N-methoxycarbonylamidino)phenyl]-5-(4-tert.-butoxycarbonylmethyl-piperazinomethyl)-2-oxazolidinone, m.p. 181°;
with 3-[4-(N-ethoxycarbonylamidino)phenyl]-5-chloromethyl-2-oxazolidinone 3-[4-(N-ethoxycarbonylamidino)phenyl]-5-(4-tert.-butoxycarbonylmethyl-piperazinomethyl)-2-oxazolidinone.

Example 39

In analogy to Example 17 by reductive cleavage of the 5-phenyl-1,2,4-oxadiazoline group starting from 1-[4-(5-phenyl-1,2,4-oxadiazolin-3-yl)phenyl]-4-[4-ethoxycarbonyl-piperidinol piperidine [obtainable by reaction of 1-(5-phenyl-1,2,4-oxadiazolin-3-yl)-4-chloropiperidine with 1-(ethoxycarbonyl)piperazine under the conditions given in Example 1] the 1-[4-(N-benzoylamidino)phenyl]-4-[4-(ethoxycarbonyl)piperidino]-piperidine, m.p. 118–119° is obtained.

Example 40

In analogy to Example 24, the following acid derivatives are obtained by hydrolysis of 3-[4-(N-benzoylamidino)phenyl]-5-(4-ethoxycarbonylmethyl-piperazinomethyl)-2-oxazolidinone [m.p. 114°; Ex. 1] 3-[4-(N-benzoylamidino)phenyl]-5-(4-carboxymethylpiperazinomethyl)-2-oxazolidinone, bistrifluoracetate, m.p. 91°;

3-(4-(N-benzoylamidino)phenyl]-5(R)-(4-ethoxycarbonylmethyl-piperazinomethyl)-2-oxazolidinone [m.p. 150°; Ex. 1] 3-[4-(N-benzoylamidino)phenyl]-5(R)-(4-carboxymethyl-piperazinomethyl)-2-oxazolidinone, bis-trifluoracetate, m.p. 147–150°, $[\alpha]_{20}$=27,6°;

3-[4-(methoxycarbonylamidino)phenyl]-5-(4-ethoxycarbonylmethyl-piperazinomethyl)-2-oxazolidinone[m.p. 181°; Ex. 39] 3-[4-(methoxycarbonylamidino)phenyl]-5-(4-carboxymethyl-piperazinomethyl)-2-oxazolidinone, tris-trifluoracetat, m.p. 92–93°.

The following examples relate to pharmaceutical formulations:

Example A
Vials

A solution of 100 g of an active substance of the formula I and 5 g of disodium hydrogen phosphate in 3 l of double-distilled water is adjusted to pH 6.5 with 2 N hydrochloric acid, filtered sterile, dispensed into vials, lyophilized under sterile conditions and sealed sterile. Each vial contains 5 mg of active substance.

Example B
Suppositories

A mixture of 20 g of an active substance of the formula I with 100 g of soya lecithin and 1400 g of cocoa butter is melted, poured into molds and left to cool. Each suppository contains 20 mg of active substance.

Example C
Solution

A solution is prepared from 1 g of an active substance of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The pH is adjusted to 6.8, the volume is made up to 1 l and the solution is sterilized by radiation. This solution can be used in the form of eyedrops.

Example D
Ointment 500 mg of an active substance of the formula I are mixed with 99.5 g of petrolatum under aseptic conditions.

Example E
Tablets

A mixture of 1 kg of active substance of the formula I, 4 kg of lactose, 1.2 kg of potato starch, 0.2 kg of talc and 0.1 kg of magnesium stearate is compressed to tablets in a conventional way such. that each tablet contains 10 mg of active substance.

Example F
Coated Tablets

Tablets are compressed in analogy to Example E and are then provided in a conventional way with a coating of sucrose, potato starch, talc, tragacanth and colorant.

Example G
Capsules 2 kg of active substance of the formula I are packed in hard gelatin capsules in a conventional way so that each capsule contains 20 mg of the active substance.

Example H
Ampoules

A solution of 1 kg of active substance of the formula I in 60 l of double-distilled water is filtered sterile, dispensed into ampoules, lyophilized under sterile conditions and sealed sterile. Each ampoule contains 10 mg of active substance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula I

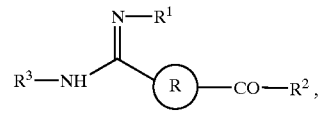

in which

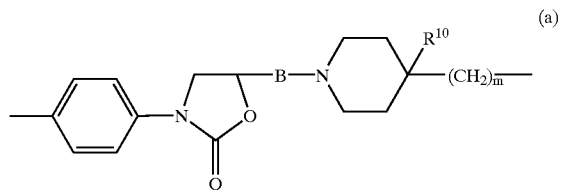

with
B=$CH_2$, CO or CS, $R^{10}$=OH or H and
m=0, 1, 2, 3 or 4; or

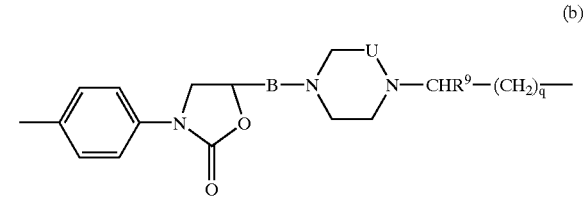

with
B=$CH_2$, CO or CS, U=$CH_2$ or CO and
$R^9$=H, $CO_2H$ or $CO_2A$, and q=0, 1, 2 or 3;
$R^1$ is H, A, Ar—CO, A—CO, OH, OA or AO—CO;
$R^2$ is OH, OA, OAr, OHet, NHOH, $NH_2$, NHA or $NA_2$;
$R^3$ is A—CO, Ar—CO, Het—CO, Het—O—CO, Ar—O—CO, A—O—CO, Ar—$SO_2$ or A—$SO_2$;
A is alkyl with 1 to 6 C atoms;
Ar is aryl of 6 to 10 C atoms, or diphenylmethyl or benzyl which are unsubstituted or substituted once, twice or three times by A, F, Cl, Br, I, OA, —O—$CH_2$—O—, COOA, COOH, $CF_3$, OH, $NO_2$, CN, $NH_2$, O—CO—A, NHA or $NA_2$; and
Het is a mono- or binuclear saturated, unsaturated or aromatic heterocycle with 1 to 4 N, O and/or S atoms, which can be unsubstituted or substituted once by F, Cl, Br, $CF_3$, A, OH, OA, CN or $NO_2$, and their physiologically acceptable salts and solvates.

2. A compound of the formula I according to claim 1 which is an enantiomer or diastereomer.

3. A compound which is:
(a) 3-p-(N-benzoylamidino)phenyl-5-[4-(ethoxycarbonylmethyl)piperazinomethyl]-2-oxazolidinone; or
(b) 3-p-(3-pyridylcarbonylamidino)phenyl-5-[4-(ethoxycarbonylmethyl)piperazinomethyl]-2-oxazolidinone;
(c) 3-p-(N-methyl-4-piperidyloxycarbonyl-amidino) phenyl-5-[4-(ethoxycarbonylmethyl)-piperazinomethyl]-2-oxazolidinone;
(d) 3-p-(N-methylsulfonylamidino)phenyl-5-[4-(carboxyethylpiperazinomethyl]-2-oxazolidinone;
(e) 3-p-(N-1-naphthoylamidino)phenyl-5-[4-(carboxyethylpiperazinomethyl]-2-oxazolidinone;
(f) 3-p-[N-(ethoxycarbonylmethylcarbamoyl)-amidino]phenyl-5-[4-(tert-butoxycarbonyl-ethyl)piperazinomethyl]-2-oxazolidinone;
(g) 3-p-[N-methylsulfonylamidino]phenyl-5-[4-(tert-butoxycarbonylethyl)piperazinomethyl]-2-oxazolidinone.

4. A process for the production of a pharmaceutical formulation, comprising combining a integrin inhibiting effective amount of a compound of the formula I according to claim 1 and/or one of its physiologically acceptable salts together with at least one solid, liquid or semiliquid vehicle or ancillary substance into a suitable administration form.

5. A pharmaceutical formulation comprising a intergrin inhibiting effective amount of at least one compound of the formula I according to claim 1, and/or one of its physiologically acceptable salts.

6. A method for controlling or treating a disease associated with undesired integrin binding comprising administering an integrin inhibiting effective amount of a compound of the formula I of claim 1 or one of its physiologically acceptable salts.

7. The method of claim 6, wherein the disease is controlled or treated by action of the compound to prevent development of blood platelet thrombi.

8. The method of claim 6, wherein the disease is controlled or treated by action of the compound to prevent undesired vessel development.

9. The method of claim 6, wherein the disease is controlled or treated by action of the compound to inhibit metastasis of tumor cells.

10. The method of claim 6, wherein the disease is controlled or treated by action of the compound to inhibit the binding of fibrinogen to the corresponding receptor.

11. The compound of formula I of claim 1 wherein R is of the formula (a), B is $CH_2$ and $R^{10}$ is H.

12. The compound of formula I of claim 1 wherein R is of the formula (b), B is $CH_2$, $R^9$ is H and q is 0 or 1.

13. The compound of claim 12, wherein U is $CH_2$ and $R^1$ is hydrogen.

14. The compound of formula I of claim 1 wherein R is of the formula (b), B is $CH_2$, U is $CH_2$ and q is 1 or 2.

15. The compound of formula I of claim 1 wherein R is of the formula (a), B is $CH_2$, m is 0 or 1 and $R^1$ is hydrogen.

16. A method for the treatment of thromboses, stroke, myocardial infarct, angina pectoris, osteoporosis, restenosis after angioplasty, ischemias, inflammations, arteriosclerosis, acute kidney failure or tumors by prevention of tumor metastasis which comprises administering a treatment effective amount of a compound of the formula I

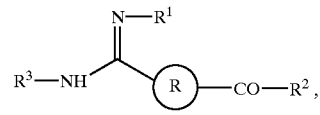

in which

R is

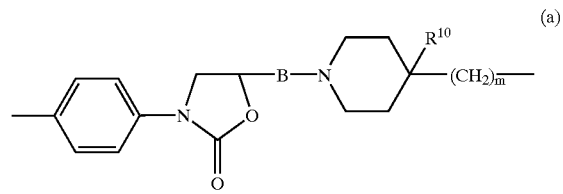

with

B=$CH_2$, CO or CS, $R^{10}$=OH or H and m=0, 1, 2, 3 or 4; or

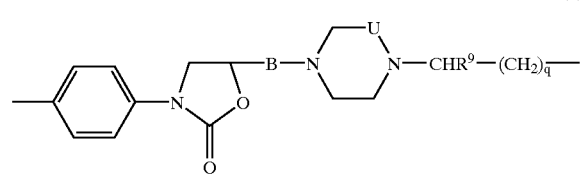

with

B=$CH_2$, CO or CS, U=$CH_2$ or CO and $R^9$=H, $CO_2H$ or $CO_2A$, and q=0, 1, 2 or 3;

$R^1$ is H, A, Ar—CO, A—CO, OH, OA or AO—CO;

$R^2$ is OH, OA, OAr, OHet, NHOH, $NH_2$ NHA or $NA_2$;

$R^3$ is A—CO, Ar—CO, Het—CO, Het—O—CO, Ar—O—CO, A—O—CO, Ar—$SO_2$ or A—$SO_2$;

A is alkyl with 1 to 6 C atoms;

Ar is aryl of 6 to 10 C atoms, or diphenylmethyl or benzyl which are unsubstituted or substituted once, twice or three times by A, F, Cl, Br, I, OA, —O—$CH_2$—O, COOA, COOH, $CF_3$, OH, $NO_2$, CN, $NH_2$, O—CO—A, NHA or $NH_2$; and Het is a mono- or binuclear saturated, unsaturated or aromatic heterocycle with 1 to 4 N, O and/or S atoms, which can be unsubstituted or substituted once by F, Cl, Br, $CF_3$, A, OH, OA, CN or $NO_2$, or one of its physiologically acceptable salts or solvates.

17. The method of claim 16, wherein the treatment is for stroke, myocardial infarct, restenosis after angioplasty, arteriosclerosis or prevention of tumor metastasis.

* * * * *

UNITED STATES PATENT AND TRADEMARK OFFICE
CERTIFICATE OF CORRECTION

PATENT NO.    : 6,455,529 B1
DATED         : September 24, 2002
INVENTOR(S)   : Gante et al.

It is certified that error appears in the above-identified patent and that said Letters Patent is hereby corrected as shown below:

<u>Column 48,</u>
Line 27, reads "in which" should read -- in which R is --

<u>Column 49,</u>
Line 26, reads "combining a integrin" should read -- combining an integrin --
Line 32, reads "comprising a intergrin" should read -- comprising an integrin --

Signed and Sealed this

Fifteenth Day of June, 2004

JON W. DUDAS
*Acting Director of the United States Patent and Trademark Office*